United States Patent
Schlingloff et al.

(10) Patent No.: US 8,044,013 B2
(45) Date of Patent: *Oct. 25, 2011

(54) USE OF METAL COMPLEX COMPOUNDS AS OXIDATION CATALYSTS

(75) Inventors: Gunther Schlingloff, Riehen (CH); Torsten Wieprecht, Schopfheim (DE); Frank Bachmann, Freiburg (DE); Josée Dannacher, Basel (CH); Marie-Josée Dubs, Wittersdorf (FR); Menno Hazenkamp, Riehen (CH); Grit Hänsler-Richter, Neuenburg (DE); Brigitte Schmidt, Lörrach (DE); Albert Schneider, Weil am Rhein (DE); Peter Weingartner, Diegten (CH)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/288,382

(22) Filed: Oct. 20, 2008

(65) Prior Publication Data

US 2009/0068282 A1 Mar. 12, 2009

Related U.S. Application Data

(62) Division of application No. 11/497,444, filed on Aug. 1, 2006, now Pat. No. 7,456,285, which is a division of application No. 10/476,043, filed as application No. PCT/EP02/04572 on Apr. 25, 2002, now Pat. No. 7,161,005.

(30) Foreign Application Priority Data

Apr. 30, 2001 (EP) .................................... 01810425
Dec. 13, 2001 (CH) .................................... 2278/01

(51) Int. Cl.
C11D 7/32 (2006.01)
C11D 7/38 (2006.01)
C11D 7/54 (2006.01)
B08B 3/04 (2006.01)

(52) U.S. Cl. ........ 510/311; 510/238; 510/372; 510/376; 510/500; 510/504; 510/505; 252/186.33; 502/200; 502/324; 502/325; 8/111; 8/137

(58) Field of Classification Search .................. 510/311, 510/372, 376, 500, 504, 505, 238; 252/186.33; 502/200, 324, 325; 8/111, 137
See application file for complete search history.

(56) References Cited

U.S. PATENT DOCUMENTS

| 4,960,895 | A | | 10/1990 | Ohkawa ........................ 546/257 |
| 5,387,719 | A | * | 2/1995 | Kneuper et al. .............. 568/455 |
| 5,453,450 | A | * | 9/1995 | Kinzer et al. ................... 522/18 |
| 5,916,481 | A | * | 6/1999 | Willey ...................... 252/186.21 |
| 7,161,005 | B2 | * | 1/2007 | Schlingloff et al. .............. 546/2 |
| 7,494,964 | B2 | * | 2/2009 | Schlingloff et al. .......... 510/311 |
| 2003/0171446 | A1 | * | 9/2003 | Murrer et al. .................... 522/16 |

FOREIGN PATENT DOCUMENTS

| DE | 4316180 | | 11/1994 |
| EP | 0867428 | | 9/1998 |
| FR | 2677766 | | 12/1992 |
| WO | 91/19730 | | 12/1991 |
| WO | 99/56699 | | 11/1999 |
| WO | 00/66536 | | 11/2000 |
| WO | 01/46368 | | 6/2001 |
| WO | WO01/46368 | * | 6/2001 |

OTHER PUBLICATIONS

Lowe et al., Beilstein Registry No. 8321073, Mar. 7, 2000.
Constable et al., Beilstein Registry No. 3613386, Oct. 23, 1991.
Chernega et al., Beilstein Registry No. 7885102, Jul. 15, 1998.
Lowe et al., Beilstein Registry No. 8333092, Mar. 7, 2000.
Lowe et al., Beilstein Registry No. 8323838, Mar. 7, 2000.
Kickelbick et al., "Structural comparison, etc.," New. J. Chem., (2002), vol. 26, pp. 462-468.
Matyjaszewski et al., "Tridenttate Nitrogen, etc.," Macromolecules, (2001), vol. 34, pp. 430-440.

* cited by examiner

*Primary Examiner* — Gregory Delcotto
(74) *Attorney, Agent, or Firm* — Shiela A. Loggins

(57) ABSTRACT

The present invention relates to the use of metal complex compounds with terpyridine ligands as oxidation catalysts. The present invention relates also to formulations comprising such metal complex compounds, to novel metal complex compounds, and to novel ligands. The metal complex compounds are used especially tor improving the action of peroxides, for example in the treatment of textile material, without at the same time causing any appreciable damage to fibres and dyeings.

14 Claims, No Drawings

USE OF METAL COMPLEX COMPOUNDS AS OXIDATION CATALYSTS

This application is a divisional of application Ser. No. 11/497,444, filed on Aug. 1, 2006 now U.S. Pat. No. 7,456, 285, which is a divisional of application Ser. No. 10/476,043, filed on Oct. 28, 2003 now U.S. Pat. No. 7,161,005, which is the National Stage of International Application PCT/EP02/04572, filed Apr. 25, 2002, all of which are herein incorporated by reference.

The present invention relates to the use of metal complex compounds with terpyridine ligands as oxidation catalysts. The present invention relates also to formulations comprising such metal complex compounds, to novel metal complex compounds and to novel ligands.

The metal complex compounds are used especially for improving the action of peroxides, for example in the treatment of textile material, without at the same time causing any appreciable damage to fibres and dyeings.

Peroxide-containing bleaching agents have been used in washing and cleaning processes for some time. They have an excellent action at a liquor temperature of 90° C. and above, but their performance noticeably decreases with lower temperatures. It is known that various transition metal ions, added in the form of suitable salts, or coordination compounds containing such cations catalyse the decomposition of $H_2O_2$. In that way it is possible to increase the bleaching action of $H_2O_2$, or of precursors that release $H_2O_2$, or of other peroxo compounds, the bleaching action of which is unsatisfactory at lower temperatures. Particularly significant for practical purposes are those combinations of transition metal ions and ligands the peroxide activation of which is manifested in an increased tendency towards oxidation in respect of substrates and not only in a catalase-like disproportionation. The latter activation, which tends rather to be undesirable in the present case, could impair the bleaching effects of $H_2O_2$ and its derivatives which are insufficient at low temperatures.

In respect of $H_2O_2$ activation having effective bleaching action, mononuclear and polynuclear variants of manganese complexes with various ligands, especially with 1,4,7-trimethyl-1,4,7-triazacyclononane and optionally oxygen-containing bridge ligands, are currently regarded as being especially effective. Such catalysts have adequate stability under practical conditions and, with $Mn^{n+}$, contain an ecologically acceptable metal cation, but their use is unfortunately associated with considerable damage to dyes and fibres.

The aim of the present invention was, therefore, to provide improved metal complex catalysts for oxidation processes which fulfil the above demands and, especially, improve the action of peroxy compounds in an extremely wide range of fields of use without giving rise to any appreciable damage.

The invention accordingly relates to the use of metal complex compounds of formula $$[L_nMe_mX_p]^zY_q \quad (1)$$

wherein Me is manganese, titanium, iron, cobalt, nickel or copper,
X is a coordinating or bridging radical,
n and m are each independently of the other an integer having a value of from 1 to 8,
p is an integer having a value of from 0 to 32,
z is the charge of the metal complex,
Y is a counter-ion,
q=z/(charge Y), and
L is a ligand of formula

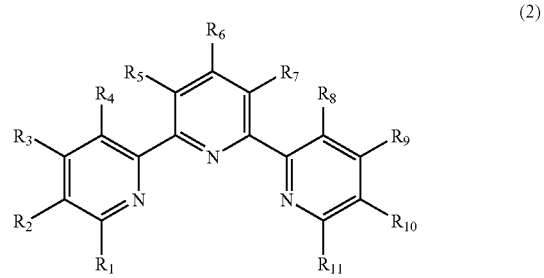

wherein
$R_1$, $R_2$, $R_3$, $R_4$, $R_5$, $R_6$, $R_7$, $R_8$, $R_9$, $R_{10}$ and $R_{11}$ are each independently of the others hydrogen; unsubstituted or substituted $C_1$-$C_{18}$alkyl or aryl; cyano; halogen; nitro; —$COOR_{12}$ or —$SO_3R_{12}$ wherein $R_{12}$ is in each case hydrogen, a cation or unsubstituted or substituted $C_1$-$C_{18}$alkyl or aryl; —$SR_{13}$, —$SO_2R_{13}$ or —$OR_{13}$ wherein $R_{13}$ is in each case hydrogen or unsubstituted or substituted $C_1$-$C_{18}$alkyl or aryl; —$N(R_{13})$—$NR'_{13}R''_{13}$ wherein $R_{13}$, $R'_{13}$ and $R''_{13}$ are as defined above for $R_{13}$; —$NR_{14}R_{15}$ or —$N^{\oplus}R_{14}R_{15}R_{16}$ wherein $R_{14}$, $R_{15}$ and $R_{16}$ are each independently of the other(s) hydrogen or unsubstituted or substituted $C_1$-$C_{18}$alkyl or aryl, or $R_{14}$ and $R_{15}$ together with the nitrogen atom bonding them form an unsubstituted or substituted 5-, 6- or 7-membered ring which may optionally contain further hetero atoms;
with the proviso that $R_1$, $R_2$, $R_3$, $R_4$, $R_5$, $R_6$, $R_7$, $R_8$, $R_9$, $R_{10}$ and $R_{11}$ are not simultaneously hydrogen,
as catalysts for oxidation reactions.

The mentioned $C_1$-$C_{18}$alkyl radicals are generally, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and more especially $C_1$-$C_4$alkyl radicals. The mentioned alkyl radicals can be unsubstituted or substituted e.g. by hydroxyl, $C_1$-$C_4$alkoxy, sulfo or by sulfato, especially by hydroxyl. The corresponding unsubstituted alkyl radicals are preferred. Very special preference is given to methyl and ethyl, especially methyl.

Examples of aryl radicals that generally come into consideration are phenyl or naphthyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthoxy. Preferred substituents are $C_1$-$C_4$alkyl, $C_1$-$C_4$alkoxy, phenyl and hydroxy. Special preference is given to the corresponding phenyl radicals.

Halogen is generally especially chlorine, bromine or fluorine, special preference being given to chlorine.

Examples of cations that generally come into consideration are alkali metal cations, such as lithium, potassium and especially sodium, alkaline earth metal cations, such as magnesium and calcium, and ammonium cations. The corresponding alkali metal cations, especially sodium, are preferred.

Suitable metal ions for Me are e.g. manganese in oxidation states II-V, titanium in oxidation states III and IV, iron in oxidation states I to IV, cobalt in oxidation states I to III, nickel in oxidation states I to III and copper in oxidation states I to III, with special preference being given to manganese, especially manganese in oxidation states II to IV, preferably in oxidation state II. Also of interest are titanium IV, iron II-IV, cobalt II-III, nickel II-III and copper II-III, especially iron II-IV.

For the radical X there come into consideration, for example, $CH_3CN$, $H_2O$, $F^-$, $Cl^-$, $Br^-$, $HOO^-$, $O_2^{2-}$, $O^{2-}$, $R_{17}COO^-$, $R_{17}O^-$, $LMeO^-$ and $LMeOO^-$, wherein $R_{17}$ is hydrogen or unsubstituted or substituted $C_1$-$C_{18}$alkyl or aryl, and $C_1$-$C_{18}$alkyl, aryl, L and Me have the definitions and preferred meanings given hereinabove and hereinbelow. $R_{17}$ is especially hydrogen, $C_1$-$C_4$alkyl or phenyl, more especially hydrogen.

As counter-ion Y there come into consideration, for example, $R_{17}COO^-$, $ClO_4^-$, $BF_4^-$, $PF_6^-$, $R_{17}SO_3^-$, $R_{17}SO_4^-$, $SO_4^{2-}$, $NO_3^-$, $F^-$, $Cl^-$, $Br^-$ and $I^-$, wherein $R_{17}$ is hydrogen or unsubstituted or substituted $C_1$-$C_{18}$alkyl or aryl. $R_{17}$ as $C_1$-$C_{18}$alkyl or aryl has the definitions and preferred meanings given hereinabove and hereinbelow. $R_{17}$ is especially hydrogen, $C_1$-$C_4$alkyl or phenyl, more especially hydrogen. The charge of the counter-ion Y is accordingly preferably 1– or 2–, especially 1–.

n is preferably an integer having a value of from 1 to 4, preferably 1 or 2 and especially 1.

m is preferably an integer having a value of 1 or 2, especially 1.

p is preferably an integer having a value of from 0 to 4, especially 2.

z is preferably an integer having a value of from 8– to 8+, especially from 4– to 4+ and more especially from 0 to 4+. z is more especially the number 0.

q is preferably an integer from 0 to 8, especially from 0 to 4 and is more especially the number 0.

$R_{12}$ is preferably hydrogen, a cation, $C_1$-$C_{12}$alkyl, or phenyl unsubstituted or substituted as indicated above. $R_{12}$ is especially hydrogen, an alkali metal cation, alkaline earth metal cation or ammonium cation, $C_1$-$C_4$alkyl or phenyl, more especially hydrogen or an alkali metal cation, alkaline earth metal cation or ammonium cation.

$R_{13}$, $R'_{13}$ and $R''_{13}$ are preferably hydrogen, $C_1$-$C_{12}$alkyl, or phenyl unsubstituted or substituted as indicated above. $R_{13}$, $R'_{13}$ and $R''_{13}$ are especially hydrogen, $C_1$-$C_4$alkyl or phenyl, more especially hydrogen or $C_1$-$C_4$alkyl, preferably hydrogen. Examples of the radical of the formula —$N(R_{13})$—$NR'_{13}R''_{13}$ that may be mentioned include —$N(CH_3)$—$NH_2$ and especially —$NH$—$NH_2$. Examples of the radical of the formula —$OR_{13}$ that may be mentioned include hydroxyl and $C_1$-$C_4$alkoxy, such as methoxy and especially ethoxy.

When $R_{14}$ and $R_{15}$ together with the nitrogen atom bonding them form a 5-, 6- or 7-membered ring it is preferably an unsubstituted or $C_1$-$C_4$alkyl-substituted pyrrolidine, piperidine, piperazine, morpholine or azepane ring. The piperazine ring can be substituted by $C_1$-$C_4$alkyl e.g. at the nitrogen atom not bonded to the phenyl radical. In addition, $R_{14}$, $R_{15}$ and $R_{16}$ are preferably hydrogen, unsubstituted or hydroxyl-substituted $C_1$-$C_{12}$alkyl, or phenyl unsubstituted or substituted as indicated above. Special preference is given to hydrogen, unsubstituted or hydroxyl-substituted $C_1$-$C_4$alkyl or phenyl, especially hydrogen or unsubstituted or hydroxyl-substituted $C_1$-$C_4$alkyl, preferably hydrogen. Examples of the radical of formula —$NR_{14}R_{15}$ that may be mentioned include —$NH_2$, —$NHCH_2CH_2OH$, —$N(CH_2CH_2OH)_2$, —$N(CH_3)CH_2CH_2OH$, and the pyrrolidine, piperidine, piperazine, morpholine or azepane ring and also 4-methyl-piperazin-1-yl.

Preference is given to ligands of formula (2) wherein $R_6$ is not hydrogen.

$R_6$ is preferably $C_1$-$C_{12}$alkyl; phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthoxy; cyano; halogen; nitro; —$COOR_{12}$ or —$SO_3R_{12}$ wherein $R_{12}$ is in each case hydrogen, a cation, $C_1$-$C_{12}$alkyl, or phenyl unsubstituted or substituted as indicated above; —$SR_{13}$, —$SO_2R_{13}$ or —$OR_{13}$ wherein $R_{13}$ is in each case hydrogen, $C_1$-$C_{12}$alkyl, or phenyl unsubstituted or substituted as indicated above; —$N(R_{13})$—$NR'_{13}R''_{13}$ wherein $R_{13}$, $R'_{13}$ and $R''_{13}$ are as defined above for $R_{13}$; —$NR_{14}R_{15}$ or —$N^{\oplus}R_{14}R_{15}R_{16}$ wherein $R_{14}$, $R_{15}$ and $R_{16}$ are each independently of the other(s) hydrogen, unsubstituted or hydroxyl-substituted $C_1$-$C_{12}$alkyl, or phenyl unsubstituted or substituted as indicated above, or $R_{14}$ and $R_{15}$ together with the nitrogen atom bonding them form an unsubstituted or $C_1$-$C_4$alkyl-substituted pyrrolidine, piperidine, piperazine, morpholine or azepane ring.

$R_6$ is especially phenyl unsubstituted or substituted by $C_1$-$C_4$alkyl, $C_1$-$C_4$alkoxy, halogen, phenyl or by hydroxyl; cyano; nitro; —$COOR_{12}$ or —$SO_3R_{12}$ wherein $R_{12}$ is in each case hydrogen, a cation, $C_1$-$C_4$alkyl or phenyl; —$SR_{13}$, —$SO_2R_{13}$ or —$OR_{13}$ wherein $R_{13}$ is in each case hydrogen, $C_1$-$C_4$alkyl or phenyl; —$N(CH_3)$—$NH_2$ or —$NH$—$NH_2$; amino; N-mono- or N,N-di-$C_1$-$C_4$-alkylamino unsubstituted or substituted by hydroxy in the alkyl moiety; or an unsubstituted or $C_1$-$C_4$alkyl-substituted pyrrolidine, piperidine, piperazine, morpholine or azepane ring.

$R_6$ is very especially $C_1$-$C_4$alkoxy; hydroxy; phenyl unsubstituted or substituted by $C_1$-$C_4$alkyl, $C_1$-$C_4$alkoxy, phenyl or by hydroxy; hydrazino; amino; N-mono- or N,N-di-$C_1$-$C_4$alkylamino unsubstituted or substituted by hydroxy in the alkyl moiety; or an unsubstituted or $C_1$-$C_4$alkyl-substituted pyrrolidine, piperidine, piperazine, morpholine or azepane ring.

Especially important as radicals $R_6$ are $C_1$-$C_4$alkoxy; hydroxy; hydrazino; amino; N-mono- or N,N-di-$C_1$-$C_4$alkylamino unsubstituted or substituted by hydroxy in the alkyl moiety; or the unsubstituted or $C_1$-$C_4$alkyl-substituted pyrrolidine, piperidine, piperazine, morpholine or azepane ring.

Very especially important as radicals $R_6$ are $C_1$-$C_4$alkoxy; hydroxy; N-mono- or N,N-di-$C_1$-$C_4$alkylamino substituted by hydroxy in the alkyl moiety; or the unsubstituted or $C_1$-$C_4$alkyl-substituted pyrrolidine, piperidine, piperazine, morpholine or azepane ring, hydroxyl being of particular interest.

The preferred meanings indicated above for $R_6$ apply also to $R_1$, $R_2$, $R_3$, $R_4$, $R_5$, $R_7$, $R_8$, $R_9$, $R_{10}$ and $R_{11}$, but those radicals may additionally denote hydrogen.

In accordance with one embodiment of the present invention, $R_1$, $R_2$, $R_3$, $R_4$, $R_5$, $R_7$, $R_8$, $R_9$, $R_{10}$ and $R_{11}$ are hydrogen and $R_6$ is a radical other than hydrogen having the definitions and preferred meanings indicated above.

In accordance with a further embodiment of the present invention, $R_1$, $R_2$, $R_4$, $R_5$, $R_7$, $R_8$, $R_{10}$ and $R_{11}$ are hydrogen and $R_3$, $R_6$ and $R_9$ are radicals other than hydrogen having the definitions and preferred meanings indicated above for $R_6$.

Preferred ligands L are those of formula

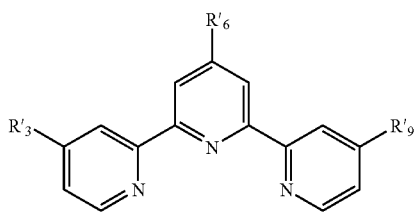
(3)

wherein R'$_3$ and R'$_9$ have the definitions and preferred meanings indicated above for R$_3$ and R$_9$, and R'$_6$ has the definitions and preferred meanings indicated above for R$_6$.

R'$_3$, R'$_6$ and R'$_9$ are preferably each independently of the others C$_1$-C$_4$alkoxy; hydroxy; phenyl unsubstituted or substituted by C$_1$-C$_4$alkyl, C$_1$-C$_4$alkoxy, phenyl or by hydroxy; hydrazino; amino; N-mono- or N,N-di-C$_1$-C$_4$alkylamino unsubstituted or substituted by hydroxy in the alkyl moiety; or an unsubstituted or C$_1$-C$_4$alkyl-substituted pyrrolidine, piperidine, piperazine, morpholine or azepane ring.

The metal complex compounds of formula (1) are known or can be obtained analogously to known processes. They are obtained in a manner known per se by reacting at least one ligand of formula (2) in the desired molar ratio with a metal compound, especially a metal salt, such as the chloride, to form the corresponding metal complex. The reaction is carried out, for example, in a solvent, such as water or a lower alcohol, such as ethanol, at a temperature of e.g. from 10 to 60° C., especially at room temperature.

Ligands of formula (2) that are substituted by hydroxyl can also be formulated as compounds having a pyridone structure in accordance with the following scheme (illustrated here using the example of a terpyridine substituted by hydroxyl in the 4'-position):

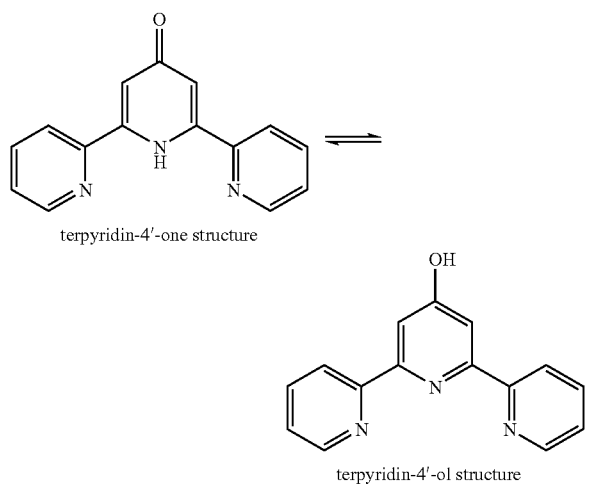

terpyridin-4'-one structure terpyridin-4'-ol structure

Their special place within the terpyridine family results from the fact that such ligands are capable of being deprotonated and are therefore able to act as anionic ligands.

Generally, therefore, hydroxyl-substituted terpyridines are also to be understood as including those having a corresponding pyridone structure.

The ligands of formula (2) are known or can be prepared in a manner known per se. For that purpose, for example, two parts of pyridine-2-carboxylic acid ester and one part of acetone can be reacted with sodium hydride and the intermediate, a 1,3,5-triketone, obtained after aqueous working-up can be reacted with ammonium acetate to synthesise the central pyridine ring. The corresponding pyridone derivatives are obtained, which can be converted into the chlorine compounds by reaction with a chlorinating agent, such as PCl$_5$/POCl$_3$. Reactions of such compounds with amines, if desired in the presence of an excess of redox-active transition metal salts, such as iron or ruthenium, in order to accelerate the substitution, yield amine-substituted terpyridines. Such preparation processes are described, for example, in J. Chem. Soc., Dalton Trans. 1990, 1405-1409 (E. C. Constable et al.) and New. J. Chem. 1992, 16, 855-867.

It has now been found that for the accelerated substitution of halide by amine at the terpyridine structure it is also possible to use catalytic amounts of non-transition metal salts, such as zinc(II) salts, which considerably simplifies the reaction procedure and working-up.

The present invention relates also to novel metal complex compounds of formula $$[L_n Me_m X_p]^z Y_q \qquad (1a),$$

wherein Me is manganese, titanium, iron, cobalt, nickel or copper,
X is a coordinating or bridging radical,
n and m are each independently of the other an integer having a value of from 1 to 8,
p is an integer having a value from 0 to 32,
z is the charge of the metal complex,
Y is a counter-ion,
q=z/(charge Y), and
L is a ligand of formula

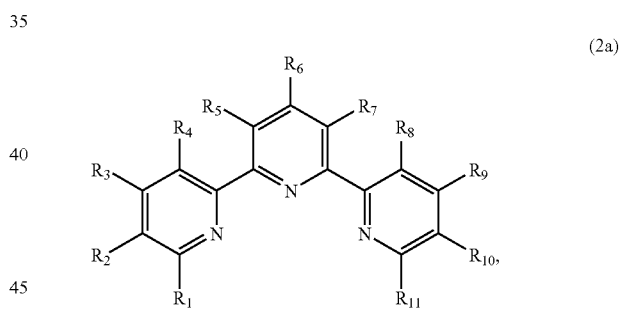
(2a)

wherein
R$_6$ is unsubstituted or substituted C$_1$-C$_{18}$alkyl; cyano; halogen; nitro; —COOR$_{12}$ or —SO$_3$R$_{12}$ wherein R$_{12}$ is in each case hydrogen, a cation or unsubstituted or substituted C$_1$-C$_{18}$alkyl or aryl; —SR$_{13}$, —SO$_2$R$_{13}$ or —OR$_{13}$ wherein R$_{13}$ is in each case hydrogen or unsubstituted or substituted C$_1$-C$_{18}$alkyl or aryl; —N(R$_{13}$)—NR'$_{13}$R"$_{13}$ wherein R$_{13}$, R'$_{13}$ and R"$_{13}$ are as defined above for R$_{13}$; —NR$_{14}$R$_{15}$ or —N$^{\oplus}$R$_{14}$R$_{15}$R$_{16}$ wherein R$_{14}$, R$_{15}$ and R$_{16}$ are each independently of the other(s) hydrogen or unsubstituted or substituted C$_1$-C$_{18}$alkyl or aryl, or R$_{14}$ and R$_{15}$ together with the nitrogen atom bonding them form an unsubstituted or substituted 5-, 6- or 7-membered ring which may optionally contain further hetero atoms; and
R$_1$, R$_2$, R$_3$, R$_4$, R$_5$, R$_7$, R$_8$, R$_9$, R$_{10}$ and R$_{11}$ are each independently of the others as defined above for R$_6$ or are hydrogen or unsubstituted or substituted aryl, with the proviso that when Me is titanium, iron, cobalt, nickel or copper, R$_3$ and R$_9$ are not hydrogen and the three radicals R$_3$, R$_6$ and R$_9$ do not have identical meanings.

The definitions and preferred meanings given above for the compounds of formula (1) apply also to the metal complex compounds of formula (1a).

The ligand L of the metal complex compounds of formula (1a) is especially a compound of formula

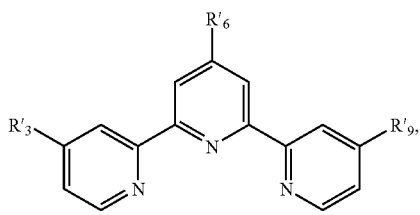

(3)

wherein $R'_6$ is $C_1$-$C_{12}$alkyl; cyano; halogen; nitro; —COOR$_{12}$ or —SO$_3$R$_{12}$ wherein R$_{12}$ is in each case hydrogen, a cation, $C_1$-$C_{12}$alkyl, or phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthoxy; —SR$_{13}$, —SO$_2$R$_{13}$ or —OR$_{13}$ wherein R$_{13}$ is in each case hydrogen, $C_1$-$C_{12}$alkyl, or phenyl unsubstituted or substituted as indicated above; —N(R$_{13}$)—NR'$_{13}$R''$_{13}$ wherein R$_{13}$, R'$_{13}$ and R''$_{13}$ are as defined above for R$_{13}$; —NR$_{14}$R$_{15}$ or —N$^\oplus$R$_{14}$R$_{15}$R$_{16}$ wherein R$_{14}$, R$_{15}$ and R$_{16}$ are each independently of the other(s) hydrogen, unsubstituted or hydroxyl-substituted $C_1$-$C_{12}$alkyl, or phenyl unsubstituted or substituted as indicated above, or R$_{14}$ and R$_{15}$ together with the nitrogen atom bonding them form an unsubstituted or $C_1$-$C_4$alkyl-substituted pyrrolidine, piperidine, piperazine, morpholino or azepane ring; and R'$_{13}$ and R'$_9$ are as defined above or are hydrogen or phenyl unsubstituted or substituted as indicated above. The definitions and preferred meanings indicated above for R'$_6$ and R'$_3$ and R'$_9$ likewise apply here.

The present invention relates also to the novel ligands of formula

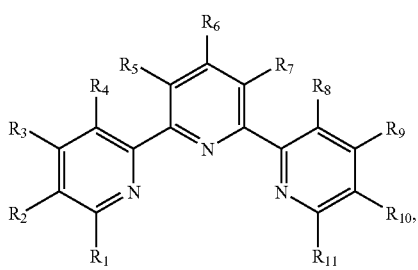

(2b)

wherein

R$_6$ is cyano; halogen; nitro; —COOR$_{12}$ or —SO$_3$R$_{12}$ wherein R$_{12}$ is in each case hydrogen, a cation or unsubstituted or substituted $C_1$-$C_{18}$alkyl or aryl; —SR$_{13}$, —SO$_2$R$_{13}$ or —OR$_{13}$ wherein R$_{13}$ is in each case hydrogen or unsubstituted or substituted $C_1$-$C_{18}$alkyl or aryl; —N(R$_{13}$)—NR'$_{13}$R''$_{13}$ wherein R$_{13}$, R'$_{13}$ and R''$_{13}$ are as defined above for R$_{13}$; —NR$_{14}$R$_{15}$ or —N$^\oplus$R$_{14}$R$_{15}$R$_{16}$ wherein R$_{14}$, R$_{15}$ and R$_{16}$ are each independently of the other(s) hydrogen or unsubstituted or substituted $C_1$-$C_{18}$alkyl or aryl, or R$_{14}$ and R$_{15}$ together with the nitrogen atom bonding them form an unsubstituted or substituted 5-, 6- or 7-membered ring which may optionally contain further hetero atoms; and R$_1$, R$_2$, R$_3$, R$_4$, R$_5$, R$_7$, R$_8$, R$_9$, R$_{10}$ and R$_{11}$ are each independently of the others as defined above for R$_6$ or are hydrogen or unsubstituted or substituted $C_1$-$C_{18}$alkyl or aryl, with the proviso that the three radicals R$_3$, R$_6$ and R$_9$ do not have identical meanings.

The definitions and preferred meanings indicated above for the ligands of formula (2) also apply here.

Preference is given to ligands of formula

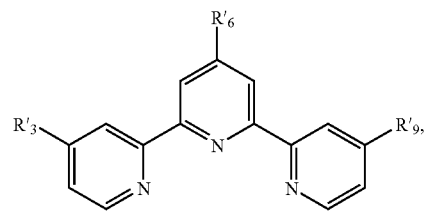

(3)

wherein

R'$_6$ is cyano; halogen; nitro; —COOR$_{12}$ or —SO$_3$R$_{12}$ wherein R$_{12}$ is in each case hydrogen, a cation, $C_1$-$C_{12}$alkyl, or phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthoxy; —SR$_{13}$, —SO$_2$R$_{13}$ or —OR$_{13}$ wherein R$_{13}$ is in each case hydrogen, $C_1$-$C_{12}$alkyl, or phenyl unsubstituted or substituted as indicated above;

—N(R$_{13}$)—NR'$_{13}$R''$_{13}$ wherein R$_{13}$, R'$_{13}$ and R''$_{13}$ are as defined above for R$_{13}$; —NR$_{14}$R$_{15}$ or —N$^\oplus$R$_{14}$R$_{15}$R$_{16}$ wherein R$_{14}$, R$_{15}$ and R$_{16}$ are each independently of the other(s) hydrogen, unsubstituted or hydroxyl-substituted $C_1$-$C_{12}$alkyl, or phenyl unsubstituted or substituted as indicated above, or R$_{14}$ and R$_{15}$ together with the nitrogen atom bonding them form an unsubstituted or $C_1$-$C_4$alkyl-substituted pyrrolidine, piperidine, piperazine, morpholine or azepane ring; and R'$_3$ and R'$_9$ are as defined above or are hydrogen, $C_1$-$C_{12}$alkyl, or phenyl unsubstituted or substituted as indicated above. The definitions and preferred meanings indicated above for R'$_6$ and R'$_3$ and R'$_9$ for the ligands of the metal complex compounds of formula (1) likewise apply here.

The metal complex compounds of formula (1) are preferably used together with peroxy compounds. Examples that may be mentioned in that regard include the following uses:

a) the bleaching of spots or stains on textile material in the context of a washing process;
b) the prevention of redeposition of migrating dyes during the washing of textile material;
c) the cleaning of hard surfaces, especially table- and kitchenware or glass;
d) the cleaning of hard surfaces, especially wall tiles or floor tiles, more especially for removing mold stains;
e) use in washing and cleaning solutions having an antibacterial action;
f) as pretreatment agents for bleaching textiles;
g) as catalysts in selective oxidation reactions in the context of organic synthesis.

A further use relates to the use of the metal complex compounds of formula (1) as catalysts for reactions with peroxy compounds for bleaching in the context of paper-making.

This relates especially to the bleaching of pulp, which can be carried out in accordance with customary processes. Also of interest is the use of the metal complex compounds of formula (1) as catalysts for reactions with peroxy compounds for the bleaching of waste printed paper.

Preference is given to the bleaching of spots or stains on textile material, the prevention of the redeposition of migrating dyes in the context of a washing process, or the cleaning of hard surfaces, especially table- or kitchen-ware or glass. For those purposes it is preferable to use aqueous formulations of the metal complex compounds of formula (1).

It should be emphasised that the metal complex compounds do not cause any appreciable damage to fibres and dyeings, for example in the bleaching of textile material.

Processes for preventing the redeposition of migrating dyes in a washing liquor are usually carried out by adding to the washing liquor, which contains a peroxide-containing washing agent, one or more metal complex compounds of formula (1) in an amount of from 0.1 to 200 mg, preferably from 1 to 75 mg, especially from 3 to 50 mg, per litre of washing liquor. It will be understood that in such an application, as well as in the other applications, the metal complex compounds of formula (1) can alternatively be formed in situ, the metal salt (e.g. manganese(II) salt, such as manganese(II) chloride) and the ligand being added in the desired molar ratios.

The present invention relates also to a washing, cleaning, disinfecting or bleaching agent, containing I) 0-50%, preferably 0-30%, A) of an anionic surfactant and/or B) of a non-ionic surfactant,
II) 0-70%, preferably 0-50%, C) of a builder substance,
III) 1-99%, preferably 1-50%, D) of a peroxide or a peroxide-forming substance, and
IV) E) a metal complex compound of formula (1) in an amount which, in the liquor, gives a concentration of 0.5-50 mg/litre of liquor, preferably 1-30 mg/litre of liquor, when from 0.5 to 20 g/litre of the washing, cleaning, disinfecting and bleaching agent are added to the liquor.

The above percentages are in each case percentages by weight, based on the total weight of the agent. The agents preferably contain from 0.005 to 2% of a metal complex compound of formula (1), especially from 0.01 to 1% and preferably from 0.05 to 1%.

When the agents according to the invention comprise a component A) and/or B), the amount thereof is preferably 1-50%, especially 1-30%.

When the agents according to the invention comprise a component C), the amount thereof is preferably 1-70%, especially 1-50%. Special preference is given to an amount of from 5 to 50% and especially an amount of from 10 to 50%.

Corresponding washing, cleaning, disinfecting or bleaching processes are usually carried out by using an aqueous liquor comprising a peroxide and from 0.1 to 200 mg of one or more compounds of formula (1) per litre of liquor. The liquor preferably contains from 1 to 30 mg of the compound of formula (1) per litre of liquor.

The agents according to the invention can be, for example, a peroxide-containing complete washing agent or a separate bleaching additive. A bleaching additive is used for removing coloured stains on textiles in a separate liquor before the clothes are washed with a bleach-free washing agent. A bleaching additive can also be used in a liquor together with a bleach-free washing agent.

The washing or cleaning agent according to the invention can be in solid or liquid form, for example in the form of a liquid, non-aqueous washing agent, comprising not more than 5% by weight water, preferably comprising from 0 to 1% by weight water, and, as base, a suspension of a builder substance in a non-ionic surfactant, e.g. as described in GB-A-2 158 454.

The washing or cleaning agent is preferably in the form of a powder or, especially, granules.

The latter can be prepared, for example, by first preparing an initial powder by spray-drying an aqueous suspension containing all the components listed above except for components D) and E), and then adding the dry components D) and E) and mixing everything together. It is also possible to add component E) to an aqueous suspension containing components A), B) and C), then to carry out spray-drying and then to mix component D) with the dry mass.

It is also possible to start with an aqueous suspension that contains components A) and C), but none or only some of component B). The suspension is spray-dried, then component E) is mixed with component B) and added, and then component D) is mixed in the dry state.

It is also possible to mix all the components together in the dry state.

The anionic surfactant A) can be, for example, a sulfate, sulfonate or carboxylate surfactant or a mixture thereof. Preferred sulfates are those having from 12 to 22 carbon atoms in the alkyl radical, optionally in combination with alkyl ethoxysulfates in which the alkyl radical has from 10 to 20 carbon atoms.

Preferred sulfonates are e.g. alkylbenzenesulfonates having from 9 to 15 carbon atoms in the alkyl radical. The cation in the case of anionic surfactants is preferably an alkali metal cation, especially sodium.

Preferred carboxylates are alkali metal sarcosinates of formula $R-CO-N(R'^1)-CH_2COOM'^1$ wherein R is alkyl or alkenyl having from 8 to 18 carbon atoms in the alkyl or alkenyl radical, $R'^1$ is $C_1$-$C_4$alkyl and $M'^1$ is an alkali metal.

The non-ionic surfactant B) can be, for example, a condensation product of from 3 to 8 mol of ethylene oxide with 1 mol of a primary alcohol having from 9 to 15 carbon atoms.

As builder substance C) there come into consideration, for example, alkali metal phosphates, especially tripolyphosphates, carbonates or hydrogen carbonates, especially their sodium salts, silicates, aluminosilicates, polycarboxylates, polycarboxylic acids, organic phosphonates, aminoalkylenepoly(alkylenephosphonates) or mixtures of those compounds.

Especially suitable silicates are sodium salts of crystalline layered silicates of the formula $NaHSi_tO_{2t+1} \cdot pH_2O$ or $Na_2Si_tO_{2t+1} \cdot pH_2O$ wherein t is a number from 1.9 to 4 and p is a number from 0 to 20.

Among the aluminosilicates, preference is given to those commercially available under the names zeolite A, B, X and HS, and also to mixtures comprising two or more of those components.

Among the polycarboxylates, preference is given to polyhydroxycarboxylates, especially citrates, and acrylates and also copolymers thereof with maleic anhydride. Preferred polycarboxylic acids are nitrilotriacetic acid, ethylenediaminetetraacetic acid and ethylenediamine disuccinate either in racemic form or in the enantiomerically pure (S,S) form.

Phosphonates or aminoalkylenepoly(alkylenephosphonates) that are especially suitable are alkali metal salts of 1-hydroxyethane-1,1-diphosphonic acid, nitrilotris(methylenephosphonic acid), ethylenediaminetetramethylenephosphonic acid and diethylenetriaminepentamethylenephosphonic acid.

As the peroxide component D) there come into consideration, for example, the organic and inorganic peroxides known in the literature and available commercially that bleach textile materials at conventional washing temperatures, for example at from 10 to 95° C.

The organic peroxides are, for example, mono- or polyperoxides, especially organic peracids or salts thereof, such as phthalimidoperoxycaproic acid, peroxybenzoic acid, diperoxydodecanedioic acid, diperoxynonanedioic acid, diperoxydecanedioic acid, diperoxyphthalic acid or salts thereof.

Preferably, however, inorganic peroxides are used, for example persulfates, perborates, percarbonates and/or persilicates. It will be understood that mixtures of inorganic and/or organic peroxides can also be used. The peroxides may be in a variety of crystalline forms and have different water contents, and they may also be used together with other inorganic or organic compounds in order to improve their storage stability.

The peroxides are added to the agent preferably by mixing the components, for example using a screw metering system and/or a fluidised bed mixer.

The agents may comprise, in addition to the combination according to the invention, one or more optical brighteners, for example from the class bis-triazinylamino-stilbenedisulfonic acid, bis-triazolyl-stilbenedisulfonic acid, bis-styrylbiphenyl or bis-benzofuranylbiphenyl, a bis-benzoxalyl derivative, bis-benzimidazolyl derivative or coumarin derivative or a pyrazoline derivative.

The agent may also comprise suspending agents for dirt, e.g. sodium carboxymethylcellulose, pH regulators, e.g. alkali metal or alkaline earth metal silicates, foam regulators, e.g. soap, salts for regulating the spray-drying and the granulating properties, e.g. sodium sulfate, perfumes and, optionally, antistatic agents and softeners, enzymes, such as amylase, bleaches, pigments and/or toning agents. Such constituents must especially be stable towards the bleaching agent used.

In addition to the bleach catalyst according to formula (1) it is also possible to use further transition metal salts or complexes known as bleach-activating active ingredients and/or conventional bleach activators, that is to say compounds that, under perhydrolysis conditions, yield unsubstituted or substituted perbenzo- and/or peroxo-carboxylic acids having from 1 to 10 carbon atoms, especially from 2 to 4 carbon atoms. Suitable bleach activators include the customary bleach activators, mentioned at the beginning, that carry O- and/or N-acyl groups having the indicated number of carbon atoms and/or unsubstituted or substituted benzoyl groups. Preference is given to polyacylated alkylenediamines, especially tetraacetylethylenediamine (TAED), acylated glycolurils, especially tetraacetylglycoluril (TAGU), N,N-diacetyl-N,N-dimethylurea (DDU), acylated triazine derivatives, especially 1,5-diacetyl-2,4-dioxohexahydro-1,3,5-triazine (DADHT), compounds of formula (4):

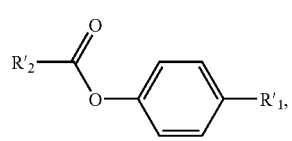
(4)

wherein $R'_1$ is a sulfonate group, a carboxylic acid group or a carboxylate group, and wherein $R'_2$ is linear or branched ($C_7$-$C_{15}$)alkyl, especially activators known under the names SNOBS, SLOBS and DOBA, acylated polyhydric alcohols, especially triacetin, ethylene glycol diacetate and 2,5-diacetoxy-2,5-dihydrofuran, and also acetylated sorbitol and mannitol and acylated sugar derivatives, especially pentaacetylglucose (PAG), sucrose polyacetate (SUPA), pentaacetylfructose, tetraacetylxylose and octaacetyllactose as well as acetylated, optionally N-alkylated glucamine and gluconolactone. It is also possible to use the combinations of conventional bleach activators known from German Patent Application DE-A-44 43 177. Nitrile compounds that form perimine acids with peroxides also come into consideration as bleach activators.

Further preferred additives to the agents according to the invention are polymers which, during the washing of textiles, prevent staining caused by dyes in the washing liquor that have been released from the textiles under the washing conditions. Such polymers are preferably polyvinylpyrrolidones or polyvinylpyridine-N-oxides which may have been modified by the incorporation of anionic or cationic substituents, especially those having a molecular weight in the range of from 5000 to 60 000, more especially from 10 000 to 50 000. Such polymers are preferably used in an amount of from 0.05 to 5% by weight, especially from 0.2 to 1.7% by weight, based on the total weight of the washing agent.

The invention relates also to granules that comprise the catalysts according to the invention and are suitable for incorporation into a powder- or granule-form washing, dishwashing, cleaning or bleaching agent. Such granules preferably comprise:

a) from 1 to 99% by weight, preferably from 1 to 40% by weight, especially from 1 to 30% by weight, of a metal complex compound of formula (1), especially of formula (1a),
b) from 1 to 99% by weight, preferably from 10 to 99% by weight, especially from 20 to 80% by weight, of a binder,
c) from 0 to 20% by weight, especially from 1 to 20% by weight, of an encapsulating material,
d) from 0 to 20% by weight of a further additive and
e) from 0 to 20% by weight of water.

As binder (b) there come into consideration anionic dispersants, non-ionic dispersants, polymers and waxes that are water-soluble, dispersible or emulsifiable in water.

The anionic dispersants used are, for example, commercially available water-soluble anionic dispersants for dyes, pigments etc.

The following products, especially, come into consideration: condensation products of aromatic sulfonic acids and formaldehyde, condensation products of aromatic sulfonic acids with unsubstituted or chlorinated diphenylene or diphenyl oxides and optionally formaldehyde, (mono-/di-)alkylnaphthalenesulfonates, sodium salts of polymerised organic sulfonic acids, sodium salts of polymerised alkylnaphthalenesulfonic acids, sodium salts of polymerised alkylbenzenesulfonic acids, alkylarylsulfonates, sodium salts of alkyl polyglycol ether sulfates, polyalkylated polynuclear arylsulfonates, methylene-linked condensation products of arylsulfonic acids and hydroxyarylsulfonic acids, sodium salts of dialkylsulfosuccinic acids, sodium salts of alkyl diglycol ether sulfates, sodium salts of polynaphthalenemethanesulfonates, lignosulfonates or oxylignosulfonates or heterocyclic polysulfonic acids.

Especially suitable anionic dispersants are condensation products of naphthalenesulfonic acids with formaldehyde, sodium salts of polymerised organic sulfonic acids, (mono-/di-)-alkylnaphthalenesulfonates, polyalkylated polynuclear arylsulfonates, sodium salts of polymerised alkylbenzenesulfonic acids, lignosulfonates, oxylignosulfonates and condensation products of naphthalenesulfonic acid with a polychloromethyldiphenyl.

Suitable non-ionic dispersants are especially compounds having a melting point of, preferably, at least 35° C. that are emulsifiable, dispersible or soluble in water, for example the following compounds:

1. fatty alcohols having from 8 to 22 carbon atoms, especially cetyl alcohol;
2. addition products of, preferably, from 2 to 80 mol of alkylene oxide, especially ethylene oxide, wherein some of the ethylene oxide units may have been replaced by substituted epoxides, such as styrene oxide and/or propylene oxide, with higher unsaturated or saturated monoalcohols, fatty acids, fatty amines or fatty amides having from 8 to 22 carbon atoms or with benzyl alcohols, phenyl phenols, benzyl phenols or alkyl phenols, the alkyl radicals of which have at least 4 carbon atoms;
3. alkylene oxide, especially propylene oxide, condensation products (block polymers);
4. ethylene oxide/propylene oxide adducts with diamines, especially ethylenediamine;
5. reaction products of a fatty acid having from 8 to 22 carbon atoms and a primary or secondary amine having at least one hydroxy-lower alkyl or lower alkoxy-lower alkyl group, or alkylene oxide addition products of such hydroxyalkyl-group-containing reaction products;
6. sorbitan esters, preferably with long-chain ester groups, or ethoxylated sorbitan esters, such as polyoxyethylene sorbitan monolaurate having from 4 to 10 ethylene oxide units or polyoxyethylene sorbitan trioleate having from 4 to 20 ethylene oxide units;
7. addition products of propylene oxide with a tri- to hexahydric aliphatic alcohol having from 3 to 6 carbon atoms, e.g. glycerol or pentaerythritol; and
8. fatty alcohol polyglycol mixed ethers, especially addition products of from 3 to 30 mol of ethylene oxide and from 3 to 30 mol of propylene oxide with aliphatic monoalcohols having from 8 to 22 carbon atoms.

Especially suitable non-ionic dispersants are surfactants of formula $$R'_{11}-O-(alkylene-O)_n-R'_{12} \quad (5),$$

wherein
$R'_{11}$ is $C_8$-$C_{22}$alkyl or $C_8$-$C_{18}$alkenyl;
$R'_{12}$ is hydrogen; $C_1$-$C_4$alkyl; a cycloaliphatic radical having at least 6 carbon atoms; or benzyl;
"alkylene" is an alkylene radical having from 2 to 4 carbon atoms and
n is a number from 1 to 60.

A substituent $R'_{11}$ or $R'_{12}$ in formula (5) is advantageously the hydrocarbon radical of an unsaturated or, preferably, saturated aliphatic monoalcohol having from 8 to 22 carbon atoms. The hydrocarbon radical may be straight-chain or branched. $R'_{11}$ and $R'_{12}$ are preferably each independently of the other an alkyl radical having from 9 to 14 carbon atoms.

Aliphatic saturated monoalcohols that come into consideration include natural alcohols, e.g. lauryl alcohol, myristyl alcohol, cetyl alcohol or stearyl alcohol, and also synthetic alcohols, e.g. 2-ethylhexanol, 1,1,3,3-tetramethylbutanol, octan-2-ol, isononyl alcohol, trimethylhexanol, trimethylnonyl alcohol, decanol, $C_9$-$C_{11}$oxo-alcohol, tridecyl alcohol, isotridecyl alcohol and linear primary alcohols (Alfols) having from 8 to 22 carbon atoms. Some examples of such Alfols are Alfol (8-10), Alfol (9-11), Alfol (10-14), Alfol (12-13) and Alfol (16-18). ("Alfol" is a registered trade mark).

Unsaturated aliphatic monoalcohols are, for example, dodecenyl alcohol, hexadecenyl alcohol and oleyl alcohol.

The alcohol radicals may be present singly or in the form of mixtures of two or more components, e.g. mixtures of alkyl and/or alkenyl groups that are derived from soybean fatty acids, palm kernel fatty acids or tallow oils.

(Alkylene-O) chains are preferably divalent radicals of the formulae

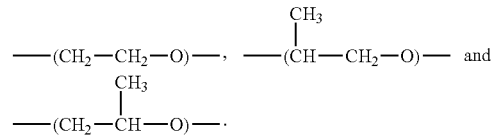

Examples of a cycloaliphatic radical are cycloheptyl, cyclooctyl and preferably cyclohexyl.

As non-ionic dispersants there come into consideration especially surfactants of formula

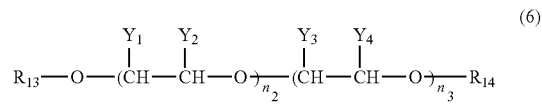

wherein
$R_{13}$ is $C_8$-$C_{22}$alkyl;
$R_{14}$ is hydrogen or $C_1$-$C_4$alkyl;
$Y_1, Y_2, Y_3$ and $Y_4$ are each independently of the others hydrogen, methyl or ethyl;
$n_2$ is a number from 0 to 8; and
$n_3$ is a number from 2 to 40.

Further important non-ionic dispersants correspond to formula

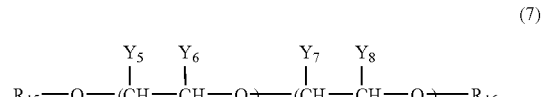

wherein
$R_{15}$ is $C_9$-$C_{14}$alkyl;
$R_{16}$ is $C_1$-$C_4$alkyl;
$Y_5, Y_6, Y_7$ and $Y_8$ are each independently of the others hydrogen, methyl or ethyl, one of the radicals $Y_5, Y_6$ and one of the radicals $Y_7, Y_8$ always being hydrogen; and
$n_4$ and $n_5$ are each independently of the other an integer from 4 to 8.

The non-ionic dispersants of formulae (5) to (7) can be used in the form of mixtures. For example, as surfactant mixtures there come into consideration non-end-group-terminated fatty alcohol ethoxylates of formula (5), e.g. compounds of formula (5) wherein
$R_{11}$ is $C_8$-$C_{22}$alkyl,
$R_{12}$ is hydrogen and
the alkylene-O chain is the radical —($CH_2$—$CH_2$—O)— and also end-group-terminated fatty alcohol ethoxylates of formula (7).

Examples of non-ionic dispersants of formulae (5), (6) and (7) include reaction products of a $C_{10}$-$C_{13}$fatty alcohol, e.g. a $C_{13}$oxo-alcohol, with from 3 to 10 mol of ethylene oxide, propylene oxide and/or butylene oxide or the reaction product of one mol of a $C_{13}$fatty alcohol with 6 mol of ethylene oxide and 1 mol of butylene oxide, it being possible for the addition products each to be end-group-terminated with $C_1$-$C_4$alkyl, preferably methyl or butyl.

Such dispersants can be used singly or in the form of mixtures of two or more dispersants.

Instead of, or in addition to, the anionic or non-ionic dispersant, the granules according to the invention may comprise a water-soluble organic polymer as binder. Such polymers may be used singly or in the form of mixtures of two or more polymers.

Water-soluble polymers that come into consideration are, for example, polyethylene glycols, copolymers of ethylene oxide with propylene oxide, gelatin, polyacrylates, polymethacrylates, polyvinylpyrrolidones, vinylpyrrolidones, vinyl acetates, polyvinylimidazoles, polyvinylpyridine-N-oxides, copolymers of vinylpyrrolidone with long-chain α-olefins, copolymers of vinylpyrrolidone with vinylimidazole, poly(vinylpyrrolidone/dimethylaminoethyl methacrylates), copolymers of vinylpyrrolidone/dimethylaminopropyl methacrylamides, copolymers of vinylpyrrolidone/dimethylaminopropyl acrylamides, quaternised copolymers of vinylpyrrolidones and dimethylaminoethyl methacrylates, terpolymers of vinylcaprolactam/vinylpyrrolidone/dimethylaminoethyl methacrylates, copolymers of vinylpyrrolidone and methacrylamidopropyl-trimethylammonium chloride, terpolymers of caprolactam/vinylpyrrolidone/dimethylaminoethyl methacrylates, copolymers of styrene and acrylic acid, polycarboxylic acids, polyacrylamides, carboxymethylcellulose, hydroxymethylcellulose, polyvinyl alcohols, polyvinyl acetate, hydrolysed polyvinyl acetate, copolymers of ethyl acrylate with methacrylate and methacrylic acid, copolymers of maleic acid with unsaturated hydrocarbons, and also mixed polymerisation products of the mentioned polymers.

Of those organic polymers, special preference is given to polyethylene glycols, carboxymethylcellulose, polyacrylamides, polyvinyl alcohols, polyvinylpyrrolidones, gelatin, hydrolysed polyvinyl acetates, copolymers of vinylpyrrolidone and vinyl acetate, and also polyacrylates, copolymers of ethyl acrylate with methacrylate and methacrylic acid, and polymethacrylates.

Suitable water-emulsifiable or water-dispersible binders also include paraffin waxes.

Encapsulating materials (c) include especially water-soluble and water-dispersible polymers and waxes. Of those materials, preference is given to polyethylene glycols, polyamides, polyacrylamides, polyvinyl alcohols, polyvinylpyrrolidones, gelatin, hydrolysed polyvinyl acetates, copolymers of vinylpyrrolidone and vinyl acetate, and also polyacrylates, paraffins, fatty acids, copolymers of ethyl acrylate with methacrylate and methacrylic acid, and polymethacrylates.

Further additives (d) that come into consideration are, for example, wetting agents, dust removers, water-insoluble or water-soluble dyes or pigments, and also dissolution accelerators, optical brighteners and sequestering agents.

The preparation of the granules according to the invention is carried out, for example, starting from:
a) a solution or suspension with a subsequent drying/shaping step or
b) a suspension of the active ingredient in a melt with subsequent shaping and solidification.

a) First of all the anionic or non-ionic dispersant and/or the polymer and, if appropriate, the further additives are dissolved in water and stirred, if desired with heating, until a homogeneous solution has been obtained. The catalyst according to the invention is then dissolved or suspended in the resulting aqueous solution. The solids content of the solution should preferably be at least 30% by weight, especially 40 to 50% by weight, based on the total weight of the solution. The viscosity of the solution is preferably less than 200 mPas.

The aqueous solution so prepared, comprising the catalyst according to the invention, is then subjected to a drying step in which all water, with the exception of a residual amount, is removed, solid particles (granules) being formed at the same time. Known methods are suitable for producing the granules from the aqueous solution. In principle, both continuous methods and discontinuous methods are suitable. Continuous methods are preferred, especially spray-drying and fluidised bed granulation processes.

Especially suitable are spray-drying processes in which the active ingredient solution is sprayed into a chamber with circulating hot air. The atomisation of the solution is effected e.g. using unitary or binary nozzles or is brought about by the spinning effect of a rapidly rotating disc. In order to increase the particle size, the spray-drying process may be combined with an additional agglomeration of the liquid particles with solid nuclei in a fluidised bed that forms an integral part of the chamber (so-called fluid spray). The fine particles (<100 µm) obtained by a conventional spray-drying process may, if necessary after being separated from the exhaust gas flow, be fed as nuclei, without further treatment, directly into the atomizing cone of the atomiser of the spray-dryer for the purpose of agglomeration with the liquid droplets of the active ingredient.

During the granulation step, the water can rapidly be removed from the solutions comprising the catalyst according to the invention, binder and further additives. It is expressly intended that agglomeration of the droplets forming in the atomising cone, or the agglomeration of droplets with solid particles, will take place.

If necessary, the granules formed in the spray-dryer are removed in a continuous process, for example by a sieving operation. The fines and the oversize particles are either recycled directly to the process (without being redissolved) or are dissolved in the liquid active ingredient formulation and subsequently granulated again.

A further preparation method according to a) is a process in which the polymer is mixed with water and then the catalyst is dissolved/suspended in the polymer solution, thus forming an aqueous phase, the catalyst according to the invention being homogeneously distributed in that phase. At the same time or subsequently, the aqueous phase is dispersed in a water-immiscible liquid in the presence of a dispersion stabiliser in order that a stable dispersion is formed. The water is then removed from the dispersion by distillation, forming substantially dry particles. In those particles, the catalyst is homogeneously distributed in the polymer matrix.

The granules according to the invention are wear-resistant, low in dust, pourable and readily meterable. They can be added directly to a formulation, such as a washing agent formulation, in the desired concentration of the catalyst according to the invention.

Where the coloured appearance of the granules in the washing agent is to be suppressed, this can be achieved, for example, by embedding the granules in a droplet of a whitish meltable substance ("water-soluble wax") or by adding a white pigment (e.g. $TiO_2$) to the granule formulation or, preferably, by encapsulating the granules in a melt consisting, for example, of a water-soluble wax, as described in EP-A-0 323 407, a white solid being added to the melt in order to reinforce the masking effect of the capsule.
b) The catalyst according to the invention is dried in a separate step prior to the melt-granulation and, if necessary, dry-ground in a mill so that all the solids particles are <50 µm in size. The drying is carried out in an apparatus customary for the purpose, for example in a paddle dryer, vacuum cabinet or freeze-dryer.

The finely particulate catalyst is suspended in the molten carrier material and homogenised. The desired granules are produced from the suspension in a shaping step with simultaneous solidification of the melt. The choice of a suitable melt-granulation process is made in accordance with the desired size of granules. In principle, any process which can be used to produce granules in a particle size of from 0.1 to 4 mm is suitable. Such processes are droplet processes (with solidification on a cooling belt or during free fall in cold air), melt-prilling (cooling medium gas/liquid), and flake formation with a subsequent comminution step, the granulation apparatus being operated continuously or discontinuously.

Where the coloured appearance of the granules prepared from a melt is to be suppressed in the washing agent, in addition to the catalyst it is also possible to suspend in the melt white or coloured pigments which, after solidification, impart the desired coloured appearance to the granules (e.g. titanium dioxide).

If desired, the granules can be covered or encapsulated in an encapsulating material. Methods suitable for such an encapsulation include the customary methods and also the encapsulation of the granules by a melt consisting e.g. of a water-soluble wax, as described, for example, in EP-A-0 323 407, coacervation, complex coacervation and surface polymerisation.

Encapsulating materials (c) include e.g. water-soluble, water-dispersible or water-emulsifiable polymers and waxes.

Further additives (d) include e.g. wetting agents, dust-removers, water-insoluble or water-soluble dyes or pigments, and also dissolution accelerators, optical brighteners and sequestering agents.

Surprisingly, the metal complex compounds of formula (1) also exhibit a markedly improved bleach-catalysing action on coloured stains on hard surfaces. The addition of such complexes in catalytic amounts to a dishwashing agent that comprises a peroxy compound and optionally TAED (N,N,N',N'-tetraacetylethylenediamine) results in the substantial removal of e.g. tea stains on china. This is the case even when hard water is used, it being known that tea deposits are more difficult to remove in hard water than in soft water. The compounds are also very suitable for cleaning hard surfaces at low temperatures.

The use of metal complex compounds of formula (1) as catalysts for reactions with peroxy compounds in cleaning solutions for hard surfaces, especially for kitchen- and tableware, is therefore of special interest.

The present invention relates also to cleaning agents for hard surfaces, especially cleaning agents for table- and kitchen-ware and, among such agents, preferably those for use in cleaning processes carried out by machine, which agents comprise one of the above-described metal complex compounds of formula (1) as bleach catalyst. Suitable formulations for such cleaning agents include, for example, the formulations mentioned above for the washing agents.

The metal complex compounds of formula (1) also have, together with peroxy compounds, excellent antibacterial action. The use of the metal complex compounds of formula (1) for killing bacteria or for protecting against bacterial attack is therefore likewise of interest.

The metal complex compounds of formula (1) are also outstandingly suitable for selective oxidation in the context of organic synthesis, especially the oxidation of organic molecules, e.g. of olefins to form epoxides. Such selective transformation reactions are required especially in process chemistry. The invention accordingly relates also to the use of the metal complex compounds of formula (1) in selective oxidation reactions in the context of organic synthesis.

The following Examples serve to illustrate the invention but do not limit the invention thereto. Parts and percentages relate to weight, unless otherwise indicated.

EXAMPLES

Synthesis of 4'-Substituted Terpyridines and 4-Pyridones

Example 1

1'H-[2,2';6',2"]Terpyridin-4'-one (Referred to as L1 Below)

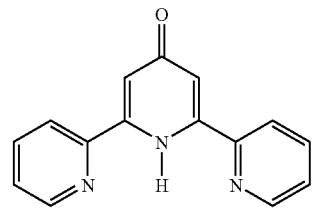

(101)

a) Step 1:
In a nitrogen atmosphere, under reflux, a solution of 20.2 ml (22.7 g, 150 mmol) of pyridine-2-carboxylic acid ethyl ester and 3.6 ml (50 mmol) of dry acetone in 100 ml of dry tetrahydrofuran is added in the course of 4 hours to a suspension of 6 g (approximately 60% dispersion in paraffin oil, about 150 mmol) of sodium hydride in 100 ml of dry tetrahydrofuran. The mixture is boiled at reflux for a further 2 hours and then concentrated using a rotary evaporator. After the addition of 200 ml of ice-water, the mixture is rendered neutral with 50% strength acetic acid and the resulting yellow 1,5-di-pyridin-2-yl-pentane-1,3,5-trione is filtered off. IR $(cm^{-1})$: 2953 (s); 2923 (vs); 2854 (m); 1605 (m); 1560 (s); 1447 (w); 1433 (w); 1374 (m); 1280 (w); 786 (w).

b) Step 2:
A mixture of 10 g (37 mmol) of 1,5-di-pyridin-2-yl-pentane-1,3,5-trione and 20 g (260 mmol) of ammonium acetate is boiled under reflux in 250 ml of ethanol for 8 hours. The mixture so obtained is concentrated to about half its volume. After filtration, 1'H-[2,2';6',2"]terpyridine-4'-one is obtained in the form of a white solid. $^1$H-NMR (360 MHz, DMSO-d6): 7.40-7.50 (qm, 2H); 7.87 (s, 2H); 7.92-8.0 (tm, 2H); 8.57 (d, 2H, 7.7 Hz); 8.68 (d, 2H, J=4.5 Hz); 10.9 (s, 1H). MS (EI pos., 70 eV), m/z=249 (100, [M$^+$]); 221 (40).
(for preparation see also K. T. Potts, D. Konwar, J. Org. Chem. 2000, 56, 4815-4816 and E. C. Constable, M. D. Ward, J. Chem. Soc. Dalton Trans. 1990, 1405-1409).

Example 2

4'-Chloro-[2,2';6',2"]terpyridine (Referred to as L2 Below)

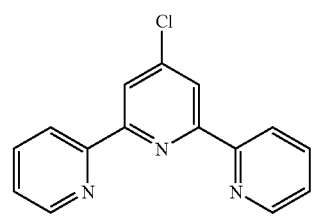

(102)

A mixture of 3.99 g (16 mmol) of 1'H-[2,2';6',2"]terpyridin-4'-one (L1) and 8.0 g (38 mmol) of phosphorus pentachloride is boiled at reflux in 200 ml of phosphorus oxychloride for sixteen hours. The mixture is allowed to cool and concentrated to dryness. 200 ml of ice-water are then added cautiously to the residue, and the solution is then adjusted to pH 9 with aqueous potassium hydroxide solution. Extraction is carried out three times using chloroform and the organic extracts are dried over sodium sulfate, filtered and concentrated. After recrystallisation from ethanol, 4'-chloro-[2,2';6',2"]terpyridine is obtained in the form of white needles.

$^1$H-NMR (CDCl$_3$, 360 MHz): 7.20-7.29 (m, 2H); 7.70-7.79 (tm, 2H); 8.37 (s, 2H); 8.47 (d, 2H, 7.6 Hz); 8.56-8.63 (dm, 2H).

(for preparation see also E. C. Constable, M. D. Ward, J. Chem. Soc. Dalton Trans. 1990, 1405-1409).

Example 3

4'-Ethoxy-[2,2';6',2"]terpyridine (Referred to as L3 Below)

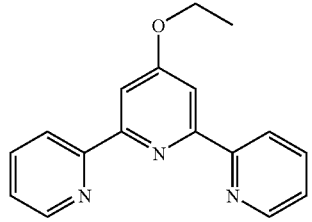

(103)

In a nitrogen atmosphere, 900 mg (3.4 mmol) of 4'-chloro-[2,2';6',2"]terpyridine are added to 15 ml of a 0.7M ethanolic sodium ethanolate solution. The mixture is heated at reflux for 20 hours. The mixture is allowed to cool and 20 ml of water are added, and 4'-ethoxy-[2,2';6',2"]terpyridine is filtered off in the form of a white solid. $^1$H-NMR (360 MHz, DMSO-d6): 1.40 (t, 3H, 6.8 Hz); 4.28 (q, 2H, 6.8 Hz); 7.42-7.53 (m, 2H); 7.93 (s, 2H); 7.95-8.02 (m, 2H); 8.58 (d, 2H, J=8.1 Hz); 8.69 (d, 2H, J=4 Hz).

(for preparation see also E. C. Constable, A. M. W. Cargill Thompson, New. J. Chem. 1992, 16, 855-867).

Example 4

[2,2';6',2"]Terpyridin-4'-yl-hydrazine (Referred to as L4 Below)

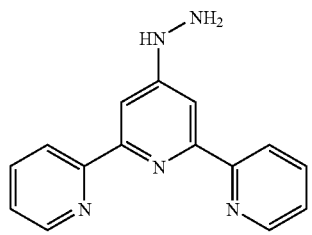

(104)

4 ml (126 mmol) of hydrazine are added to 600 mg (2.2 mmol) of 4'-chloro-[2,2';6',2"]-terpyridine in 12 ml of 2-butanol. The mixture is heated at reflux for 17 hours and cooled, and [2,2';6',2"]terpyridin-4'-yl-hydrazine is filtered off in the form of a white solid.

$^1$H-NMR (360 MHz, DMSO-d6): 4.38 (s br, 2H); 7.38-7.45 (m, 2H); 7.84 (s, 2H); 7.88-7.97 (m, 3H); 8.52-8.57 (m, 2H); 8.64-8.76 (m, 2H).

(for preparation see also G. Lowe et al., J. Med. Chem., 1999, 42, 999-1006).

Example 5

2-(Methyl-[2,2';6',2"]terpyridin-4'-yl-amino)-ethanol (Referred to as L5 Below)

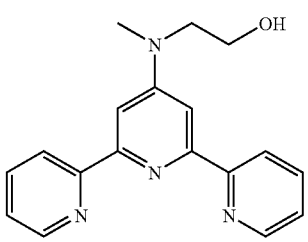

(105)

A solution in 20 ml of dichloromethane of 1.61 g (6 mmol) of 4'-chloro-2,2';6',2"-terpyridine and 20 ml of N-methylaminoethanol are added in succession to a solution of 1.35 g (6.8 mmol) of iron(II) chloride tetrahydrate in 100 ml of isopropanol. The mixture is then boiled at reflux for 20 hours. The mixture is concentrated and a solution of 1.66 g of ammonium hexafluorophosphate in 10 ml of methanol is added. The resulting violet precipitate is washed four times using 50 ml of diethyl ether each time and once with 50 ml of water. The residue is then stirred for 14 hours in a solution of 4 g of sodium hydroxide in 300 ml of water/acetonitrile (1:1 v/v) in an oxygen atmosphere. Filtration is carried out over kieselguhr and the residue is washed with 50 ml of water, 50 ml of acetonitrile and 100 ml of dichloromethane. The filtrates are concentrated. Extraction is carried out four times with dichloromethane and the combined organic extracts are dried over sodium sulfate, filtered and concentrated. The residue is recrystallised from acetone/petroleum ether and acetonitrile; 2-(methyl-[2,2';6',2"]terpyridin-4'-yl-amino)-ethanol is obtained in the form of a white solid. MS (ESI pos., KF), m/z=345 (100, [M+K]$^+$); 307 (35, [M+H]$^+$).

(for preparation see also G. Lowe et al., J. Med. Chem., 1999, 42, 999-1006).

Example 6

4'-Pyrrolidin-1-yl-[2,2';6',2"]terpyridine (Referred to as L6 Below)

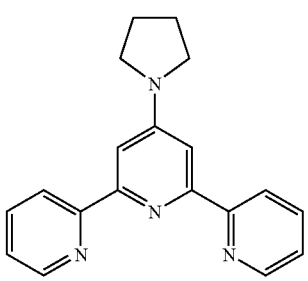

(106)

28 mg (<5 mol %) of zinc(II) chloride and 4.4 g (61.5 mmol) of pyrrolidine are added in succession to a mixture of 1.1 g (4.1 mmol) of 4'-chloro-[2,2';6',2"]terpyridine in 15 ml of 2-methyl-2-butanol. The mixture is heated at reflux for 20 hours, cooled and filtered. After recrystallisation from toluene, pure 4'-pyrrolidin-1-yl-[2,2';6',2"]terpyridine is obtained in the form of a white solid. MS (EI, 70 eV): m/z=303 (15); 302 (90, [M+]); 273 (100); 233 (25).

$^1$H-NMR (360 MHz, CDCl$_3$): 1.9-2.0 (m, 4H); 3.39-3.49 (m, 4H); 7.18 (dd, 2H, J=6.7, 5.2 Hz); 7.51 (s, 2H); 7.66-7.76 (tm, 2H); 8.51 (d, 2H, J=7.7 Hz); 8.54-8.60 (m, 2H).

Example 7

2-[(2-Hydroxy-ethyl)-[2,2';6',2"]terpyridin-4'-yl-amino]-ethanol (Referred to as L7 Below)

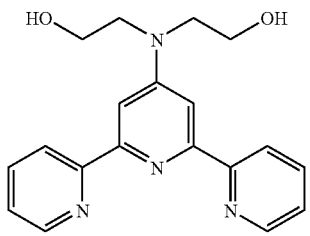

(107)

3.41 g (17.2 mmol) of manganese(II) chloride tetrahydrate and 98 g (0.93 mol) of diethanolamine are added in succession to a mixture of 2.14 g (8 mmol) of 4'-chloro-[2,2';6',2"]-terpyridine in 200 ml of methanol. The mixture is heated at reflux for 14 hours, cooled and concentrated. The residue so obtained is stirred in 250 ml of sodium hydroxide solution in acetonitrile/water 1:1 (v/v, pH>12) for 20 hours in air. Acetonitrile is removed using a rotary evaporator and the aqueous portion is extracted three times with chloroform. The organic extract is filtered over sodium sulfate and concentrated. Diethyl ether is added to the residue and the mixture is stirred and filtered, yielding 2-[(2-hydroxy-ethyl)-[2,2';6',2"]-terpyridin-4'-yl-amino]-ethanol in the form of a white solid. $^1$H-NMR (360 MHz, CD$_3$OD): 3.76 (t, J=5.4 Hz, 4H); 3.85 (t, J=5.4 Hz, 4H); 7.38-7.47 (tm, 2H); 7.69 (s, 2H); 7.94 (dt, J=8.1, 1.8 Hz, 2H); 8.53 (d, J=8.1 Hz, 2H); 8.58-8.65 (dm, 2H).

Example 8

4'-(4-Methyl-piperazin-1-yl)-[2,2';6',2"]terpyridine (Referred to as L8 Below)

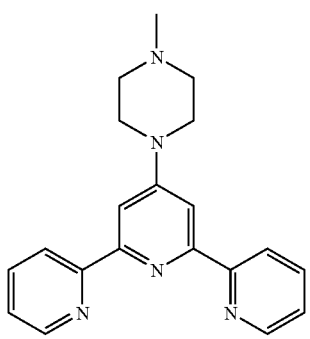

(108)

This compound is prepared analogously to the procedure indicated above for the preparation of the ligand L7 in Example 7, but 1-methylpiperazine is used as amine component. 4'-(4-Methyl-piperazin-1-yl)-[2,2';6',2"]terpyridine, white solid. $^{13}$C-NMR (90 MHz, CDCl$_3$): 157.1 (2 signals, quart.); 156.3 (quart.); 149.1 (tert.); 137.0 (tert.); 123.8 (tert); 121.6 (tert); 105.7 (tert.); 55.0 (sec.); 46.6 (sec.); 46.4 (prim.). MS (EI pos., 70 eV), m/z=331 (100, [M+]), 261 (95); 233 (40); 70 (40); 50 (43).

Example 8b 1,1-Dimethyl-4-[2,2';6',2"]terpyridin-4'-yl-piperazin-1-ium iodide (Referred to as L8b Below)

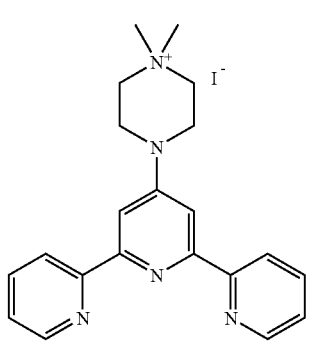

(108a)

211 mg (0.64 mmol) of ligand L8 are dissolved in 11 ml of acetonitrile and at room temperature an excess of methyl iodide (2.1 ml) is added dropwise thereto. The mixture is then stirred for 3 hours at room temperature and concentrated, and 10 ml of dichloromethane are added to the residue. The precipitate is filtered off and dried in vacuo, 1,1-dimethyl-4-[2,2';6',2"]terpyridin-4'-yl-piperazin-1-ium iodide, beige solid. $^1$H-NMR (360 MHz, CD$_3$OD): 3.34 (s, 6H), 3.62-3.80 (m, 4H); 3.85-4.03 (m, 4H); 7.39-7.52 (m, 2H); 7.86-8.03 (m, 4H); 8.57 (d, J=7.7 Hz, 2H); 8.63 (d, J=4.5 Hz, 2H).

Example 9

4'-Azepan-1-yl-[2,2';6',2"]terpyridine (Referred to as L9 Below)

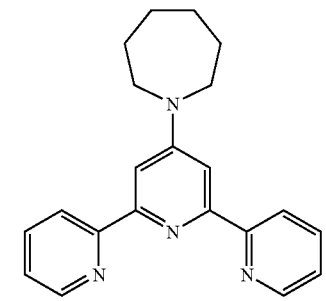

(109)

This compound is prepared analogously to the procedure indicated above for the preparation of the ligand L7 in Example 7, but hexamethyleneimine is used as amine component. 4'-Azepan-1-yl-[2,2';6',2"]terpyridine, white solid. $^{13}$C-NMR (90 MHz, CDCl$_3$): 157.7 (quart.); 156.1 (quart.); 155.6 (quart.); 149.2 (tert.); 137.0 (tert.); 123.7 (tert.); 121.8 (tert); 103.7 (tert); 49.4 (sec); 27.9 (sec); 27.4 (sec). MS (EI pos., 70 eV), m/z=330 (100, [M+]); 287 (45); 273 (25); 233 (20).

Example 10

4'-Piperidin-1-yl-[2,2';6',2"]terpyridine (Referred to as L10 Below)

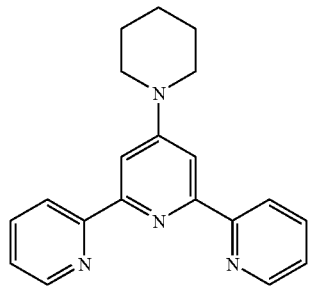
(110)

This compound is prepared analogously to the procedure indicated above for the preparation of the ligand L7 in Example 7, but piperidine is used as amine component. 4'-Piperidin-1-yl-[2,2';6',2"]terpyridine, white solid. $^{13}$C-NMR (CDCl$_3$): 157.4 (quart.); 157.3 (quart.); 156.2 (quart.); 149.2 (tert.); 137.1 (tert.); 123.8 (tert); 121.8 (tert.); 105.7 (tert.); 48.1 (sec.); 25.9 (sec.); 24.9 (sec.). MS (EI pos., 70 eV), m/z=316 (100, [M$^+$]); 287 (35); 261 (25); 233 (70).

Example 11

4'-Morpholin-4-yl-[2,2';6',2"]terpyridine (Referred to as L11 Below)

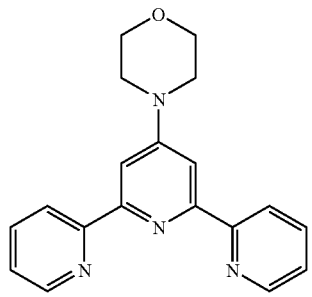
(111)

This compound is prepared analogously to the procedure indicated above for the preparation of the ligand L7 in Example 7, but morpholine is used as amine component. 4'-Morpholin-4-yl-[2,2';6',2"]terpyridine, white solid. $^{13}$C-NMR (CDCl$_3$): 157.6 (quart.); 157.0 (quart.); 156.5 (quart.); 149.2 (tert.); 137.2 (tert.); 124.0 (tert.); 121.8 (tert.); 105.7 (tert.); 67.0 (sec.); 47.0 (sec.). MS (EI pos., 70 eV), m/z=318 (100, [M$^+$]); 287 (35); 261 (45); 233 (85).

Example 12

4'-(4-tert-Butyl-phenyl)-[2,2';6',2"]terpyridine (Referred to as L12 Below)

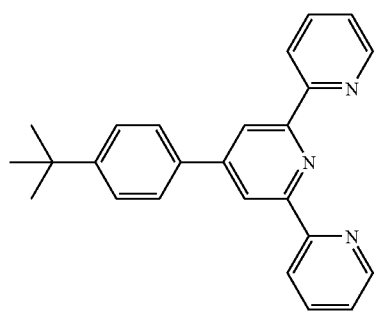
(112)

4.06 g (25 mmol) of 4-tert-butyl benzaldehyde are dissolved in 150 ml of ethanol. Sodium hydroxide solution (5.13 g in 40 ml of water) is added and then 10.54 g (87 mmol) of 2-acetylpyridine are added dropwise over a period of 10 minutes. The mixture is then stirred at room temperature for 18 hours. The pale pink precipitate so obtained is filtered with suction and washed with 10 ml each of methanol and water. A second fraction is obtained from the mother liquor by adding water. 2.54 g of the residue so obtained are then taken up in 160 ml of glacial acetic acid; 32 g (excess) of ammonium acetate are added and the mixture is heated at reflux for 3 hours. The mixture is cooled, neutralised with sodium carbonate solution and extracted twice with dichloromethane. The mixture is dried over sodium sulfate and filtered and the organic extract is concentrated. After recrystallisation from methanol, 4'-(4-tert-butyl-phenyl)-[2,2';6',2"]terpyridine is obtained in the form of a white solid. $^{13}$C-NMR (90 MHz, CDCl$_3$): 156.8 (quart.); 156.3 (quart.); 152.7 (quart.); 150.5 (quart.); 149.5 (tert.); 137.2 (tert.); 135.9 (quart.); 127.4 (tert.); 126.3 (tert.); 124.1 (tert.); 121.8 (tert.); 119.2 (tert.); 35.0 (quart.); 31.6 (prim.).

(for preparation see also E. C. Constable, P. Harveson, D. R. Smith, L. Whall, Polyhedron 1997, 16, 3615-3623).

Example 13

4'-(4-Isopropyl-phenyl)-[2,2';6',2"]terpyridine (Referred to as L13 Below)

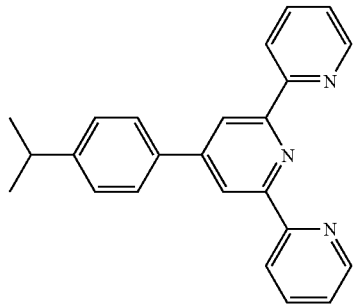
(113)

This compound is prepared analogously to the procedure described above for the preparation of the ligand L12 in Example 12, but 4-isopropyl benzaldehyde is used as carbonyl component. 4'-(4-Isopropyl-phenyl)-[2,2';6',2"]terpyridine, white solid. $^{13}$C-NMR (90 MHz, CDCl$_3$): 155.4 (quart.); 155.0 (quart.); 149.3 (quart.); 149.1 (quart.); 148.2 (tert.); 135.9 (tert.); 135.0 (quart.); 126.4 (tert.); 125.8 (tert.); 122.8 (tert.); 120.5 (tert.); 117.6 (tert.); 30.0 (tert.); 23.0 (prim.).

Example 14

4'-p-Tolyl-[2,2';6',2"]terpyridine (Referred to as L14 Below)

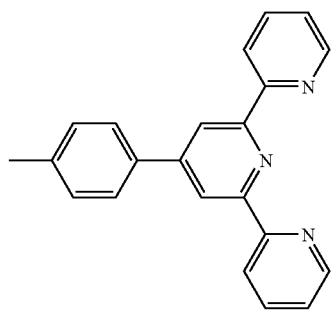
(114)

This compound is prepared analogously to the procedure described above for the preparation of the ligand L12 in Example 12, but 4-methylbenzaldehyde is used as carbonyl component. 4'-p-Tolyl-[2,2';6',2"]terpyridine, white solid. $^{13}$C-NMR (90 MHz, CDCl$_3$): 155.8 (quart.); 155.3 (quart.); 149.6 (quart.); 148.5 (tert.); 138.5 (quart.); 136.0 (tert.); 134.9 (quart.); 128.7 (tert.); 126.6 (tert.); 123.2 (tert.); 120.8 (tert.); 118.0 (tert.); 20.7 (prim.).

Example 15

4'-Biphenyl-4-yl-[2,2';6',2"]terpyridine (Referred to as L15 Below)

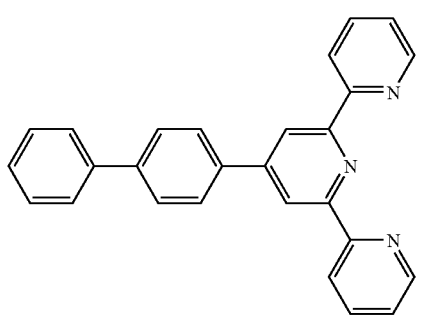

(115)

This compound is prepared analogously to the procedure described above for the preparation of the ligand L12 in Example 12, but 4-phenyl benzaldehyde is used as carbonyl component. 4'-Biphenyl-4-yl-[2,2';6',2"]terpyridine, white solid. $^{13}$C-NMR (90 MHz, CDCl$_3$): 156.6 (quart.); 156.3 (quart.); 150.0 (quart.); 149.5 (tert.); 142.2 (quart.); 140.8 (quart.); 137.6 (quart.); 136.9 (tert.); 129.3 (tert.); 128.1 (tert.); 128.0 (tert.); 127.9 (tert.); 126.3 (tert.); 124.2 (tert.); 121.8 (tert.); 119.1 (tert.).

Synthesis of Building Blocks for Polysubstituted Ligands of the Pyridone Type

Example 16

4-Chloro-pyridine-2-carboxylic acid methyl ester a) Step 1:

36.9 g (0.3 mol) of pyridine-2-carboxylic acid are dissolved in 105 ml of thionyl chloride. After the addition of 3.1 g (30 mmol) of sodium bromide, the mixture is heated cautiously to reflux temperature. Boiling is continued for 24 hours, the gases formed being removed via a wash bottle filled with sodium hydroxide solution. When the reaction is complete, the mixture is allowed to cool and concentrated using a rotary evaporator.

b) Step 2:

300 ml of methanol are cautiously added, with stirring, at 0° C. to the brown residue obtained in Step 1. The mixture is heated to room temperature and stirred for a further 30 minutes to complete the reaction. The mixture is concentrated and 750 ml of 5% strength sodium hydrogen carbonate solution are added thereto; extraction is carried out three times using ethyl acetate. The organic extracts are dried over sodium sulfate, filtered and concentrated. The crude product so obtained is distilled in a sickle flask (about 100-120° C., 0.1 mbar). 4-Chloro-pyridine-2-carboxylic acid methyl ester is obtained in the form of a white solid.

$^1$H-NMR (360 MHz, CDCl$_3$): 4.01 (s, 3H); 7.44 (dd, 1H, J=5.4, 1.8 Hz); 8.12 (d, 1H, J=1.8 Hz); 8.4 (d, 1H, J=5.4 Hz). (for preparation see also R. J. Sundberg, S. Jiang, Org. Prep. Proced. Int. 1997, 29, 117-122).

Example 17

4-Ethoxy-pyridine-2-carboxylic acid ethyl ester

This compound is obtained in a manner analogous to that described in Example 16, except that in Step 2 ethanol is used instead of methanol and the mixture is heated at reflux for 24 hours after the addition of alcohol. The purification of the crude product is effected by distillation (100-105° C., 0.08 mbar). 4-Ethoxy-pyridine-2-carboxylic acid ethyl ester is obtained in the form of a colourless oil. $^1$H-NMR (360 MHz, CDCl$_3$): 1.44 (m, 6H); 4.15 (q, 2H, J=7.0 Hz); 4.47 (q, 2H, J=7.0 Hz); 6.94 (dd, 1H, J=5.1, 2.7 Hz); 7.65 (d, 2H, J=2.7 Hz); 8.54 (d, 1H; J=5.7 Hz).

Example 18

4-Pyrrolidin-1-yl-pyridine-2-carboxylic acid ethyl ester a) Step 1:

This step is carried out in a manner analogous to that described in Step 1 in Example 16.

b) Step 2:

This step is carried out as described in T. Sammiakia, T. B. Hurley, J. Org. Chem. 2000, 65, 974-978: to the resulting crude acid chloride in dichloromethane there is added dropwise at 0° C. a dichloromethane solution of a threefold excess of pyrrolidine and catalytic amounts of N,N-dimethylaminopyridine. The mixture is then stirred for a further one hour at room temperature, then heated at reflux for 5 hours and concentrated using a rotary evaporator. The residue is then extracted five times with diethyl ether. The ethereal extracts are concentrated. The residue is then taken up in 6M hydrochloric acid and boiled at reflux for 6 hours. On concentration using a rotary evaporator, pure 4-pyrrolidin-1-yl-pyridine-2-carboxylic acid is precipitated. For the synthesis of 4-pyrrolidin-1-yl-pyridine-2-carboxylic acid ethyl ester, the carboxylic acid is taken up in thionyl chloride and heated at boiling for 30 minutes. Concentration is carried out using a rotary evaporator and the procedure is then as described in Example 16, Step 2, except that ethanol is used as alcohol.

Example 19

1,5-Bis(4-chloro-pyridin-2-yl)pentane-1,3,5-trione

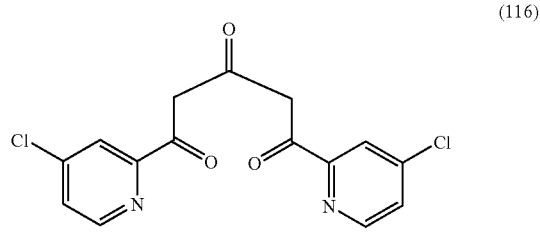

(116)

This compound is prepared in a manner analogous to that described in Example 1, Step 1, for pyridine-2-carboxylic acid ethyl ester, but instead 4-chloro-pyridine-2-carboxylic acid methyl ester from Example 16 is used. The beige solid crude product is used for further syntheses without special purification steps.

IR (cm$^{-1}$): 1619 (m); 1564 (s); 1546 (s); 1440 (m); 1374 (s); 1156 (m); 822 (w).

Example 20

1,5-Bis(4-ethoxy-pyridin-2-yl)pentane-1,3,5-trione

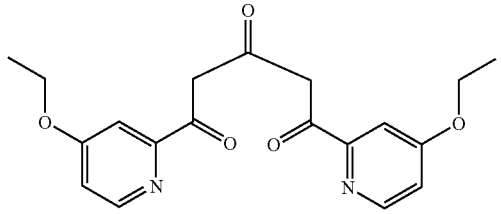

(117)

This compound is prepared in a manner analogous to that described in Example 1, Step 1, for pyridine-2-carboxylic acid ethyl ester, but instead 4-ethoxy-pyridine-2-carboxylic acid ethyl ester from Example 17 is used. The yellowish crude product is used for further syntheses without special purification steps. IR (cm$^{-1}$): 1557 (vs); 1469 (w); 1436 (w); 1300 (m); 1207 (m); 1186 (m); 1035 (m); 818 (m).

Example 21

1,5-Bis(4-pyrrolidin-1-yl-pyridin-2-yl)-pentane-1,3,5-trione

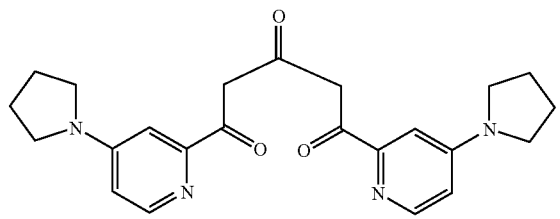

(118)

This compound is prepared in a manner analogous to that described in Example 1, Step 1, for pyridine-2-carboxylic acid ethyl ester, but instead 4-pyrrolidin-1-yl-pyridine-2-carboxylic acid ethyl ester from Example 18 is used. The yellow-orange crude product is used for further syntheses without special purification steps. IR (cm$^{-1}$): 1548 (s); 1504 (s); 1453 (s); 1381 (s); 1349 (m); 1276 (w); 1243 (M); 1207 (w); 796 (w).

Synthesis of Polysubstituted Terpyridines and Pyridones

Example 22

4,4''-Dichloro-1'H-[2,2';6',2'']terpyridin-4'-one (Referred to as L16 Below)

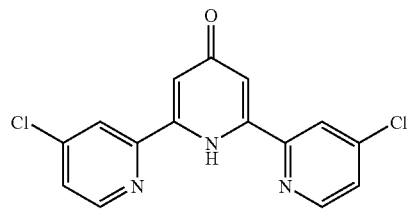

(119)

This compound is prepared in a manner analogous to that described in Example 1, Step 2, for 1,5-di-pyridin-2-yl-pentane-1,3,5-trione, but instead the chloro-substituted triketone from Example 19 is used. Pure 4,4''-dichloro-1'H-[2,2';6',2''] terpyridin-4'-one can be obtained by recrystallisation from toluene in the form of a white crystalline powder. $^{13}$C-NMR (90 MHz, CDCl$_3$): 165.6 (quart.); 156.5 (quart.); 154.9 (quart.); 150.2 (tert.); 143.6 (quart.); 123.7 (tert.); 120.2 (tert.); 108.5 (tert.).

Example 23

4,4''-Diethoxy-1'H-[2,2';6',2'']terpyridin-4'-one (Referred to as L17 Below)

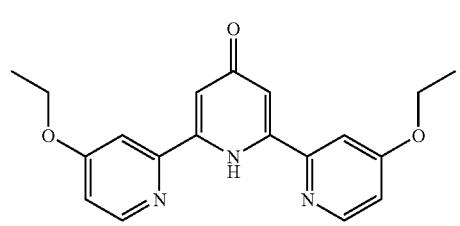

(120)

This compound is prepared in a manner analogous to that described in Example 1, Step 2 for 1,5-di-pyridin-2-yl-pentane-1,3,5-trione, but instead the ethoxy-substituted triketone from Example 20 is used. Pure 4,4''-diethoxy-1'H-[2,2';6',2''] terpyridin-4'-one can be obtained by chromatography on silica gel (chloroform/methanol 9:1, 0.1% NH$_4$OH) in the form of a white crystalline powder. $^1$H-NMR (360 MHz, CDCl$_3$): 1.37 (t, 6H, 7.2 Hz); 4.05 (q, 4H, 7.2 Hz); 6.77 (dd, 2H, J=5.9, 2.3 Hz), 6.99 (br s, 2H), 7.30 (br s, 2H); 8.42 (d, 2H, J=5.9 Hz).

MS (EI pos., 70 eV), m/z=337 (75, [M$^+$]); 322 (90); 309 (100); 281 (75); 28 (85).

Example 24

4,4"-Di-pyrrolidin-1-yl-1'H-[2,2';6',2"]terpyridin-4'-one (Referred to as L18 Below)

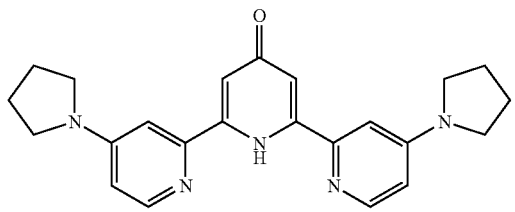
(121)

This compound is prepared in a manner analogous to that described in Example 1, Step 2 for 1,5-di-pyridin-2-yl-pentane-1,3,5-trione, but instead the pyrrolidine-substituted triketone from Example 21 is used. Pure 4,4"-di-pyrrolidin-1-yl-1'H-[2,2';6',2"]terpyridin-4'-one can be obtained by recrystallisation from methanol in the form of an almost colourless solid. 1.81-2.05 (m, 8H); 3.17-3.33 (m, 8H); 6.32 (dd, 2H, J=5.7, 2.3 Hz); 6.84 (d, 2H, J=2.3 Hz); 6.90 (s, 2H); 8.19 (d, 2H, J=5.7 Hz). MS (EI pos., 70 eV), m/z=387 ([M$^+$]), 359 (100); 358 (85); 330 (20); 28 (60).

This compound can also be obtained by heating pyrrolidine and 4,4"-dichloro-1'H-[2,2';6',2"]-terpyridin-4'-one, if desired in the presence of metal salts (see e.g. Example 6).

Example 25

4,4"-Bis[(2-hydroxy-ethyl)-methyl-amino]-1'H-[2,2';6',2"]terpyridin-4'-one (Referred to as L19 Below)

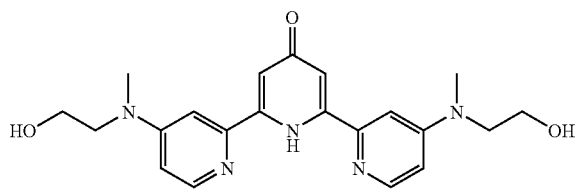
(122)

This compound is prepared in a manner analogous to that described in Example 6 for 4'-pyrrolidin-1-yl-[2,2';6',2"]terpyridine, but instead 2-(N-methylamino)ethanol is used as amine and 4,4"-dichloro-1'H-[2,2';6',2"]terpyridin-4'-one from Example 22 is used as precursor.

$^1$H-NMR (360 MHz, DMSO-d6): 3.12 (s, 6H); 3.20-4.00 (m, 8H); 6.73-6.82 (m, 2H); 7.70-7.95 (m, 4H); 8.23 (d, 2H, 5.9 Hz).

Example 26

4,4"-Diethoxy-4'-methoxy-[2,2';6',2"]terpyridine (Referred to as L20 Below)

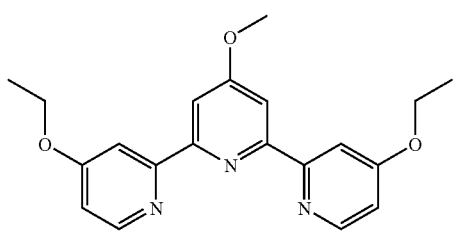
(123)

In an argon atmosphere, 506 mg (1.5 mmol) of 4,4"-diethoxy-1'H-[2,2';6',2"]terpyridin-4'-one (L17, Example 23) are added at 0° C. to a suspension of 78 mg (approximately 60% dispersion in paraffin oil, 1.95 mmol) of sodium hydride in 15 ml of absolute N,N-dimethyl-formamide. The mixture is then stirred for 15 minutes at 0° C. and for 15 minutes at room temperature. After cooling again, 0.12 ml (1.95 mmol) of methyl iodide is added. Stirring is then carried out at room temperature for a further 45 minutes. 15 ml of water are added and filtration is carried out, yielding 4,4"-diethoxy-4'-methoxy-[2,2';6',2"]terpyridine in the form of a beige powder.

$^1$H-NMR (360 MHz, CDCl$_3$): 1.39 (t, 6H, J=7.2 Hz); 3.90 (s, 3H); 4.12 (q, 4H, J=7.2 Hz); 6.73 (dd, 2H, J=5.6, 2.5 Hz); 7.88 (s, 2H); 8.01 (d, 2H, J=2.5 Hz); 8.39 (d, 2H, 5.6 Hz). MS (EI pos, 70 eV), m/z=351 (90, [M$^+$]); 350 (70); 336 (100); 323 (70); 295 (45).

Example 27

4'-Methoxy-4,4"-di-pyrrolidin-1-yl-[2,2';6',2"]terpyridine (Referred to as L21 Below)

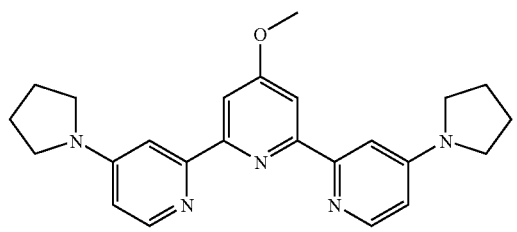
(124)

26 mg of sodium hydride dispersion (60% strength, 0.65 mmol) are suspended under argon in 5 ml of abs. N,N-dimethylformamide and cooled to 0° C. Then 193 mg (0.5 mmol) of 4,4"-di-pyrrolidin-1-yl-1'H-[2,2';6',2"]terpyridin-4'-one (L18 from Example 24) are added. The yellow suspension is stirred for 30 minutes 0° C. and then heated at room temperature for 15 minutes. The mixture is cooled again and a solution of 40 μl (0.65 mmol) of methyl iodide is added. The mixture is stirred for a further 45 minutes and the precipitate that forms is filtered off and recrystallised from methanol. 4'-Methoxy-4,4"-di-pyrrolidin-1-yl-[2,2';6',2"]-terpyridine is obtained in the form of a white solid. 168.1 (quart.); 157.9 (quart.); 156.6 (quart.); 152.9 (quart.); 149.5 (tert.); 107.4 (tert.); 107.1 (tert.); 105.0 (tert.); 55.9 (prim.); 47.3 (sec.); 25.8 (sec.). MS (EI, 70 eV), m/z: 401 (50, [M$^+$]); 373 (80); 372 (100); 332 (20); 28 (40).

Example 28

4,4',4"-Trichloro-[2,2';6',2"]terpyridine (Referred to as L22 Below)

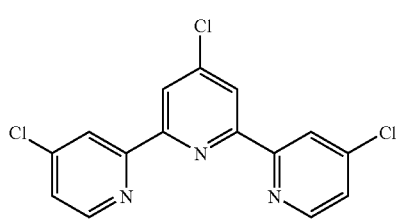
(125)

This compound is prepared in a manner analogous to that described in Example 2 for 1'H-[2,2';6',2"]terpyridin-4'-one, but instead the dichloro-substituted pyridone L16 from Example 22 is used. 4,4',4"-Trichloro[2,2';6',2"]terpyridine, white solid. $^1$H-NMR (90 MHz, CDCl$_3$): 7.24-7.31 (m, 2H), 8.38 (s, 2H); 8.45 (d, 2H, 1.8 Hz); 8.48 (d, 2H, 5.0 Hz).

Example 29

4,4',4"-Triethoxy-[2,2';6',2"]terpyridine (Referred to as L23 Below)

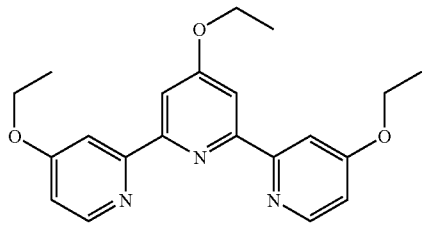
(126)

53 mg (0.15 mmol) of 4,4',4"-trichloro[2,2';6',2"]terpyridine from Example 28 are added to 2.5 ml of a 0.72M ethanolic solution. The mixture is heated at reflux for 2 hours. The mixture is cooled, 2.5 ml of water are added and the 4,4',4"-triethoxy[2,2';6',2"]terpyridine is filtered off in the form of a pale pink powder. $^{13}$C-NMR (90 MHz, CDCl$_3$): 167.4 (quart.); 166.2 (quart.); 158.4 (quart.); 157.1 (quart.); 150.7 (tert.); 110.6 (tert.); 108.1 (2 signals, tert.); 64.2 (sec.); 64.1 (2 signals, sec.); 15.0 (3 signals, prim.).

Example 30

4,4',4"-Tri-pyrrolidin-1-yl[2,2';6',2"]terpyridine (Referred to as L24 Below)

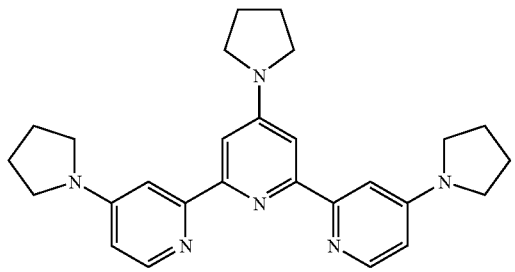
(127)

This compound is prepared in a manner analogous to that described in Example 7 with 4'-chloro-[2,2';6',2"]terpyridine, but instead the trichloro-substituted terpyridine L22 from Example 28, and pyrrolidine as amine component are used. 4,4',4"-Tri-pyrrolidin-1-yl-[2,2';6',2"]terpyridine, beige powder. MS (EI pos., 70 eV), m/z=440 (50, [M$^+$]); 412 (80); 411 (100); 371 (20); 220 (20), 28 (15). IR (cm$^{-1}$): 2850 (w); 1608 (vs); 1537 (s); 1515 (m); 1480 (m); 1458 (m); 1019 (m); 799 (m).

Example 31

2-({4',4"-Bis[(2-hydroxy-ethyl)methyl-amino]-[2,2'; 6',2"]terpyridin-4-yl}-methyl-amino)-ethanol (Referred to as L25 Below)

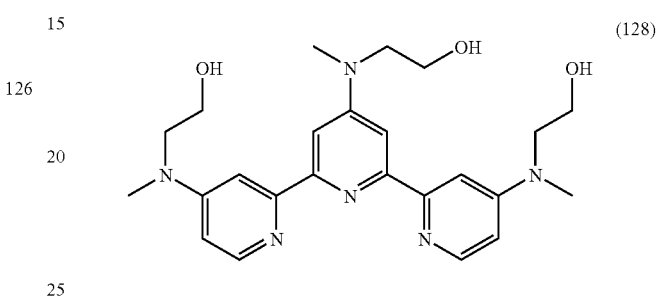
(128)

This compound is prepared in a manner analogous to that described in Example 7 with 4'-chloro-[2,2';6',2"]terpyridine, but instead the trichloro-substituted terpyridine L22 from Example 28, and 2-methylaminoethanol as amine component are used. 2-({4',4"-Bis[(2-hydroxy-ethyl)-methyl-amino]-[2, 2';6',2"]terpyridin-4-yl}-methyl-amino)-ethanol, white solid. $^{13}$C-NMR (90 MHz, DMSO-d6): 156.4 (quart.); 155.7 (quart.); 155.3 (quart.); 154.4 (quart.); 149.2 (tert.); 106.7 (tert.); 103.4 (tert.); 103.1 (tert.); 58.4 (2 signals, sec.); 58.2 (sec.); 53.6 (sec.); 53.5 (2 signals, sec.); 38.6 (prim.); 38.3 (2 signals, prim.).

Example 32

4'-Chloro-4,4"-diethoxy-[2,2';6',2"]terpyridine (Referred to as L26 Below)

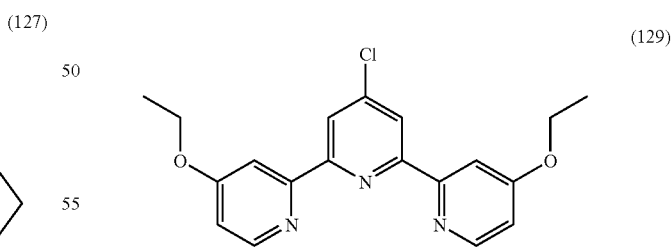
(129)

This compound is prepared in a manner analogous to that described in Example 2 for 1'H-[2,2';6',2"]terpyridin-4'-one, but instead the diethoxy-substituted pyridone L17 from Example 23 is used. 4'-Chloro-4,4"-diethoxy-[2,2';6',2"] terpyridine, white solid. $^{13}$C-NMR (90 MHz, CDCl$_3$): 166.3 (quart.); 157.0 (quart.); 156.9 (quart.); 150.8 (tert.); 146.5 (quart.); 121.7 (tert.); 110.8 (tert.); 108.4 (tert.); 64.2 (sec.); 14.9 (prim.).

Example 33

4,4''-Diethoxy-4'-pyrrolidin-1-yl-[2,2';6',2'']terpyridine (Referred to as L27 Below)

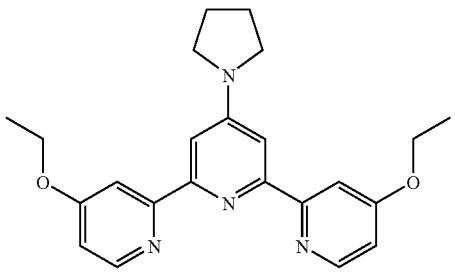

(130)

This compound is prepared in a manner analogous to that described in Example 7 with 4'-chloro-[2,2';6',2'']terpyridine, but instead the chloro-substituted terpyridine L26 from Example 32, and pyrrolidine as amine component are used. 4,4''-Diethoxy-4'-pyrrolidin-1-yl-[2,2';6',2'']terpyridine, white solid. $^{13}$C-NMR (90 MHz, CDCl$_3$): 166.2 (quart.); 159.4 (quart.); 157.1 (quart.); 155.6 (quart.); 150.4 (tert.); 110.5 (tert.); 107.9 (tert.); 104.8 (tert.); 63.9 (sec.); 47.8 (sec.); 25.8 (sec.); 15.0 (prim.). MS (EI pos., 70 eV), m/z=390 (100, [M$^+$]); 333 (70); 305 (20); 28 (25).

Example 34

2-[(4,4''-Diethoxy-[2,2';6',2'']terpyridin-4'-yl)-(2-hydroxy-ethyl)-amino]-ethanol (Referred to as L28 Below)

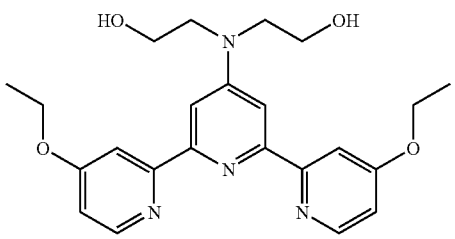

(131)

This compound is prepared in a manner analogous to that described in Example 7 with 4'-chloro-[2,2';6',2'']terpyridine, but instead the chloro-substituted terpyridine L26 from Example 32 is used as amine component. Recrystallisation from methanol yields 2-[(4,4''-diethoxy-[2,2';6',2'']terpyridin-4'-yl)-(2-hydroxy-ethyl)-amino]-ethanol in the form of a white solid. $^{13}$C-NMR (90 MHz, CDCl$_3$): 165.5 (quart.); 158.0 (quart.); 155.0 (quart.); 154.6 (quart.); 150.6 (tert.); 110.4 (tert.); 107.0 (tert.); 103.5 (tert.); 63.6 (sec.); 57.9 (sec.); 52.7 (sec.); 14.5 (prim.).

Example 35

6,6''-Bis(2-methoxyphenyl)-2,2':6':2''-terpyridine (Referred to as L29 Below)

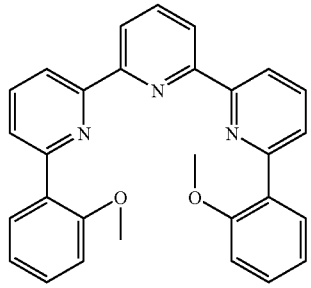

(132)

A solution of 7.6 g (24 mmol) of caesium carbonate in 8 ml of water is added to a solution of 0.9 g (2.3 mmol) of 6',6''-dibromo-2,2':6',2''-terpyridine in 14 ml of dimethoxyethane. 8.9 mg (0.02 mmol) of μ-bromo(triisopropylphosphine)(η$^3$-allyl) palladium(II) (see WO-A-99/47474) and 0.89 g (5.88 mmol) of 2-methoxyphenylboronic acid are added. The mixture is then heated at reflux under argon for 10 hours. The mixture is cooled and the phases are separated; the organic extract is extracted three times with ethyl acetate. The organic phase is dried over sodium sulfate, filtered and concentrated. The crude product is chromatographed (silica gel, hexane/ethyl acetate 10:1). 6,6''-Bis(2-methoxyphenyl)-2,2':6':2''-terpyridine, white solid. $^{13}$C-NMR (90 MHz, CDCl$_3$): 157.7 (quart.); 155.7 (quart.); 155.3 (quart.); 138.2 (tert.); 137.1 (tert.); 131.9 (tert.); 130.5 (tert.); 129.3 (quart.); 125.6 (tert.); 121.6 (tert.); 121.5 (tert.); 119.5 (tert.); 112.0 (tert.); 56.1 (prim.).

Example 36

6,6''-Bis(2-hydroxyphenyl)-2,2':6',2''-terpyridine (Referred to as L30 Below)

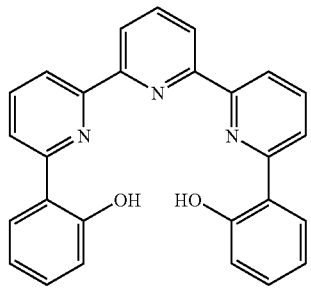

(133)

1.12 g (4.49 mmol) of boron tribromide dissolved in 5 ml of dichloromethane are added dropwise at −75° C. to a solution of 200 mg (0.448 mmol) of 6,6''-bis(2-methoxyphenyl)-2,2':6':2''-terpyridine (L29, Example 35) in 15 ml of dichloromethane. After one hour the cooling bath is removed and the solution is stirred at room temperature for 10 hours to complete the reaction. The solution is poured into ice-water and neutralised with sodium hydrogen carbonate solution. Extraction is carried out twice with dichloromethane and the combined organic extracts are dried over sodium sulfate, filtered and concentrated. The crude product is chromatographed (silica gel, dichloromethane/methanol 20:1). 6,6''-Bis(2-hydroxyphenyl)-2,2':6',2''-terpyridine, white solid.

13C-NMR (90 MHz, CDCl3): 160.2 (quart.); 157.7 (quart.); 154.5 (quart.); 153.1 (quart.); 139.4 (tert.); 139.2 (tert.); 132.1 (tert.); 130.2 (quart.); 126.9 (tert.); 121.9 (tert.); 121.6 (tert.); 120.0 (tert.); 119.5 (tert.); 119.2 (tert.); 118.9 (tert.).

Synthesis of Metal Complexes with Terpyridine Ligands and 4-Pyridone Ligands

Example 37

Manganese(II) Complex Containing a Pyridone Ligand: {[2,2';6',2"]terpyridin-4'-ol}manganese(II) chloride

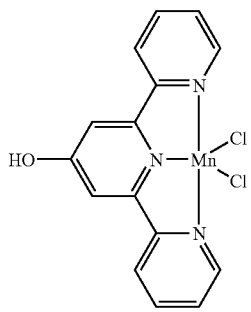

(134)

198 mg (1 mmol) of manganese(II) chloride tetrahydrate are dissolved in 10 ml of ethanol, and 249 mg (1 mmol) of 1'H-[2,2';6',2"]terpyridin-4'-one L1 are added. The mixture is stirred for 24 hours at room temperature and filtered, and the light-yellow solid is dried in vacuo. $C_{15}H_{11}Cl_2MnN_3O$, 375.12; calculated C, 48.03; H, 2.96; N, 11.20; Mn, 14.65. found C, 48.22; H, 3.14; N, 11.13; Mn, 14.6. IR (cm$^{-1}$): 3082 (br, vs), 1613 (s), 1600 (s), 1558 (s), 1429 (m), 1224 (s), 1011 (m), 798 (m).

Example 38

Manganese(II) Complex with a Substituted Terpyridine Ligand: {2-[(2-hydroxy-ethyl)-[2,2';6',2"]terpyridin-4'-yl-amino]-ethanol}manganese(II) chloride

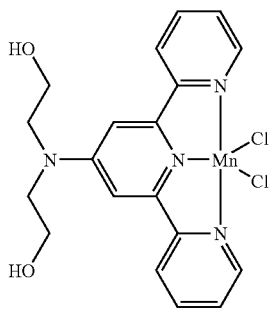

(135)

336 mg (1 mmol) of 2-[(2-hydroxy-ethyl)-[2,2';6',2"]terpyridin-4'-yl-amino]-ethanol L7 dissolved in 5 ml of water are added dropwise to 5 ml of an aqueous solution of 198 mg (1 mmol) of manganese(II) chloride tetrahydrate. The mixture is then stirred for 20 minutes at room temperature and filtered, and the light-yellow solid is dried in vacuo. $C_{19}H_{20}Cl_2MnN_4O_2$*0.11 H$_2$O; calculated C, 49.16; H, 4.39; N, 12.07; Mn, 11.83. found C, 49.23; H, 4.38; N, 12.07; Mn, 12.1. IR (cm$^{-1}$): 3512 (w), 3456 (m), 1609 (vs), 1569 (w), 1518 (s), 1532 (w), 1569 (w), 1473 (w), 1444 (s), 1055 (w), 1055 (s), 1013 (vs), 789 (vs).

Example 38a

{2-(Methyl-[2,2';6',2"]terpyridin-4'-yl-amino)-ethanol}manganese(II) chloride

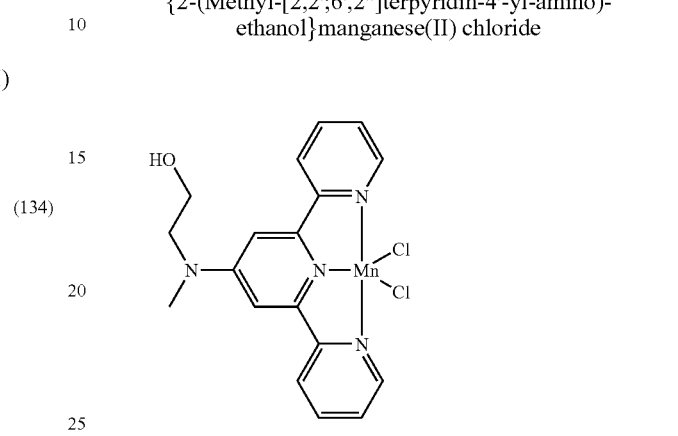

7.66 g (25 mmol) of 2-(methyl[2,2';6',2"]terpyridin-4'-yl-amino)ethanol L5 are added, in five portions, over a period of 30 minutes to 100 ml of an ethanolic manganese(II) chloride tetra-hydrate solution (4.95 g, 25 mmol). The mixture is diluted with 70 ml of ethanol, stirred for 18 hours at room temperature and filtered, and the light-yellow solid is dried in vacuo. $C_{18}H_{18}Cl_2MnN_4O$; calculated C, 50.02; H, 4.20; N, 12.96; Mn, 12.71; Cl, 16.41. found C, 49.90; H, 4.12; N, 12.78; Mn, 12.9; Cl, 16.33.

Example 39

Manganese(II) Complex with Two Substituted Terpyridine Ligands: Bis{2-[(2-hydroxy-ethyl)-[2,2';6',2"]terpyridin-4'-yl-amino]-ethanol}manganese(II) chloride

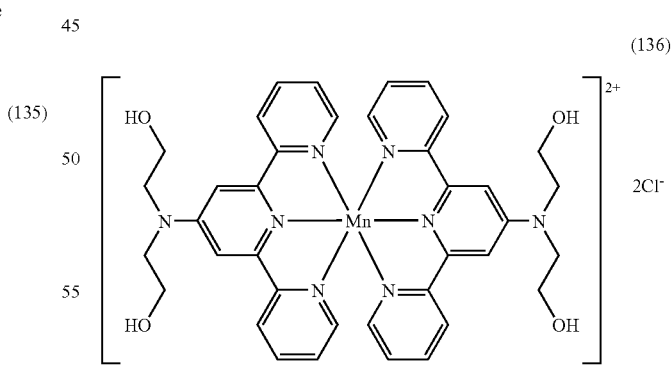

(136)

336 mg (1 mmol) of 2-[(2-hydroxy-ethyl)-[2,2';6',2"] terpyridin-4'-yl-amino]-ethanol L7 are suspended in 5 ml of ethanol/water, and an ethanolic solution of 99 mg (0.5 mmol) of manganese(II) chloride tetrahydrate is added. The mixture is stirred at room temperature for 90 minutes and filtered, and the orange-yellow solid is dried. $C_{38}H_{40}Cl_2MnN_8O_4$*H$_2$O, calculated C, 55.89; H, 5.18; N, 13.72; Mn, 6.73. found C, 56.08; H, 5.44; N, 13.58; Mn, 6.66.

IR (cm$^{-1}$): 3240 (br), 1598 (vs), 1570 (w), 1510 (m), 1473 (m), 1442 (s), 1046 (w), 1011 (vs), 792 (w).

Modification of Manganese-Bonded, Substituted Terpyridine-like Ligands, Direct Complex Synthesis:

Example 40

Bis{4,4"-bis[(2-hydroxy-ethyl)-methyl-amino]-[2,2'; 6',2"]terpyridin-4'-ol}-manganese(II) chloride 318 mg (1 mmol) of L16 are heated at reflux in 25 ml of methanol with 426 mg (2.2 mmol) of manganese(II) chloride tetrahydrate and 8.8 g (117 mmol) of N-methylaminoethanol under argon for 18 hours. The mixture is concentrated and the residue is chromatographed on silica gel (dichloromethane/methanol 4:1). $C_{42}H_{50}Cl_2MnN_{10}O_6$, yellow solid. IR (cm$^{-1}$): 3238 (br, m), 1603 (vs) 1511 (s), 1536 (m), 1484 (m), 1450 (m), 1356 (w), 1010 (s).

Synthesis of higher valency manganese complexes with substituted ligands of the terpyridine type (Examples 41 to 44) [cf. process of J. Limburg et al., Science 1999, 283, 1524-1527 for terpyridine]:

Example 41

1.78 g (7.14 mmol) of 1'H-[2,2';6',2"]terpyridin-4'-one L1 are added to a solution of 1.75 g (7.14 mmol) of manganese (II) acetate tetrahydrate in 35 ml of water. Then a solution of 3.28 g (9.93 mmol of active oxygen as KHSO$_5$) of potassium peroxomonosulfate in 20 ml of water is added dropwise thereto. The mixture is then stirred for 2 hours at room temperature, then filtered with suction and washed with 25 ml of water. Drying is carried out for 12 hours at 50° C. in vacuo, yielding 2.05 g of olive-green powder. IR (cm$^{-1}$): 3068 (m), 1613 (m), 1602 (m), 1587 (s), 1480 (m), 1099 (vs), 1053 (w), 1028 (s), 1011 (s), 788 (m).

Example 42

1.23 g (5 mmol) of manganese(II) acetate tetrahydrate are added to a suspension of 1.68 g (5 mmol) of 2-[(2-hydroxy-ethyl)-[2,2';6',2"]terpyridin-4'-yl-amino]-ethanol L7. A solution of 1.44 g (4.37 mmol of active oxygen as KHSO$_5$) of potassium peroxomonosulfate in 30 ml of water is then added dropwise. To the resulting red solution there is then added dropwise a total of 25 ml of 1M ammonium hexafluorophosphate solution. The precipitate is filtered off and washed twice using 10 ml of water each time. The red solid is then taken up in 30 ml of acetonitrile, filtered through a paper filter and concentrated. The residue that remains is extracted with dichloromethane for 16 hours in a Soxhlet apparatus and then dried at 50° C. in vacuo. 2.15 g of wine-red powder are obtained.

IR (cm$^{-1}$): 2981 (s), 2923 (s), 2866 (m), 2844 (m), 1621 (s), 1571 (w), 1537 (w), 1475 (s), 1356 (m), 1055 (s), 1032 (vs), 1011 (s), 829 (vs), 784 (s), 740 (w).

Example 43

99 mg (0.5 mmol) of manganese(II) chloride tetrahydrate are added to a suspension of 168 mg (0.5 mmol) of 2-[(2-hydroxy-ethyl)-[2,2';6',2"]terpyridin-4'-yl-amino]-ethanol L7. A solution of 144 mg (0.44 mmol of active oxygen as KHSO$_5$) of potassium peroxomonosulfate in 3 ml of water is then added dropwise. The almost black solid is filtered off and dried at 50° C. in vacuo. IR (cm$^{-1}$): 3324 (br, m), 3076 (br), 1614 (s), 1523 (w), 1476 (m), 1154 (w), 1055 (w), 1025 (vs), 925 (w), 647 (s).

Application Examples

Application Example 1

Stability of the Mn Complexes

For this purpose, 50 μmolar aqueous solutions of a complex of manganese(II) chloride tetrahydrate and a terpyridine-like ligand, dissolved in a borax buffer of pH 10.0, are prepared.

For testing the stability, the solutions are exposed at 40° C. to a hydrogen peroxide concentration of 8.6 mM for 30 minutes.

For comparison purposes, a corresponding solution of the unsubstituted terpyridine ligand is prepared (without hydrogen peroxide).

The optical density is determined by means of the respective UV/VIS spectrum at the wavelength indicated in Table 1 below and is a measure of the stability.

The Mn complex of formula (137) given in Table 1 below is the compound of formula

TABLE 1

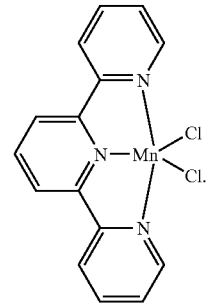

(137)

| Compound | Time | Optical density |
|---|---|---|
| Unsubstituted terpyridine | — | 0.03 (335 nm) |
| Mn complex (137) | t = 0 min. | 0.43 (335 nm) |
| Mn complex (137) | t = 30 min. (without H$_2$O$_2$) | 0.11 (335 nm) |
| Mn complex (137) | t = 30 min. (with H$_2$O$_2$) | 0.08 (335 nm) |
| Mn complex (134) | t = 0 min. | 0.60 (320 nm) |
| Mn complex (134) | t = 30 min. (without H$_2$O$_2$) | 0.60 (320 nm) |
| Mn complex (134) | t = 30 min. (with H$_2$O$_2$) | 0.60 (320 nm) |

The above Example shows that the manganese complex with substituted terpyridine has markedly greater stability in comparison with the manganese complex with unsubstituted terpyridine. In the case of the manganese complex with unsubstituted terpyridine, the complex has largely decomposed after 30 minutes, and the UV/VIS spectrum obtained is virtually the same as that of the ligand (terpyridine), whereas the manganese complex with the substituted terpyridine is stable.

Application Example 2

Bleaching Action in Washing Agents 7.5 g of white cotton fabric and 2.5 g of tea-stained cotton fabric are treated in 80 ml of washing liquor. The liquor contains a standard washing agent (ECE, 456 IEC) in a concentration of 7.5 g/l. The hydrogen peroxide concentration is 8.6 mmol/l. The catalyst concentration (1:1 complex of manganese(II) chloride tetrahydrate with the ligand in question, prepared in methanolic solution with the addition of a small amount of lithium hydroxide) is 50 μmol/l. The washing process is carried out in a steel beaker in a LINITEST apparatus for 30 minutes at 40° C. For evaluating the bleaching results, the increase in the lightness DY (difference in lightness according to CIE) of the stains brought about by the treatment is determined spectrophotometrically in comparison with values obtained without the addition of catalyst.

TABLE 2

| 1:1 Mn complex with ligand | DY increase | Ligand | DY increase |
|---|---|---|---|
| L1 | 5.0 | L10 | 4.4 |
| L4 | 5.0 | L11 | 5.5 |
| L5 | 5.2 | L17 | 5.3 |
| L6 | 5.8 | L18 | 3.0 |
| L7 | 5.6 | L19 | 5.3[1] |
| L8 | 5.0 | L25 | 6.2 |
| L8a | 4.5 | L28 | 4.3 |
| L9 | 3.8 | | |

[1] Half concentration used

As can be seen from Table 2 above, the manganese complexes exhibit a very good bleaching action.

Application Example 3

Cleaning Performance on Soiled Surfaces at 53° C.

A tea-stained cup is filled with 100 ml of a buffer solution (10 mM carbonate, pH=10.0) containing 1.1 mM of hydrogen peroxide and 7.3 μM of 1:1 manganese complex (prepared as described in Application Example 2). Using a thermostat, the temperature of the solution is raised from 23° to 53° C. over a period of 12 minutes and maintained at the final temperature for 23 minutes. After rinsing and drying in air, the results are evaluated visually on a scale of 1 (no cleaning) to 10 (clean). The catalyst-free system is used as reference.

TABLE 3

| 1:1 Manganese complex with ligand | Rating (rating of reference) | Difference |
|---|---|---|
| L1 | 5.0 (3.1) | 1.9 |
| L6 | 7.2 (3.3) | 3.9 |
| L7 | 6.9 (3.3) | 3.6 |
| L10 | 5.2 (3.1) | 2.1 |
| L11 | 5.7 (3.3) | 2.4 |
| L28 | 5.2 (3.0) | 2.2 |
| Unsubstituted terpyridine | 3.8 (3.9) | −0.1 |

Application Example 4

Cleaning Performance on Soiled Surfaces at 23° C.

The procedure is as in Application Example 3 but the cleaning is carried out at a constant temperature of 23° C. (duration: 45 minutes).

TABLE 4

| Compound used | Rating (rating of reference) | Difference |
|---|---|---|
| Manganese complex of formula (136) | 7.6 (3.8) | 3.8 |
| N,N'-tetraacetylethylenediamine (TAED), 0.16 g/l | 6.8 (3.9) | 2.9 |

TAED is a commercially available bleach activator which is included in Table 4 for comparison purposes.

Application Example 5

Decomposition of Hydrogen Peroxide

The procedure is as in Application Example 3 but the consumption of $H_2O_2$ is determined iodometrically.

TABLE 5

| 1:1 manganese complex with ligand | Residual $H_2O_2$ (mM) | Consumption (%) |
|---|---|---|
| L1 | 0.73 | 34 |
| Unsubstituted terpyridine | 0.02 | 98 |

As can be seen in Table 5, in the case of the use of the 1:1 manganese complex with the substituted terpyridine ligand the undesired decomposition of $H_2O_2$ to $O_2$ and $H_2O$ is substantially reduced.

Application Example 6

Activity of the Manganese Catalysts after the Bleaching Cycle

The procedure as described in Application Example 2 is carried out for the $1^{st}$ cycle, the cotton fabric is removed and for the $2^{nd}$ cycle the procedure is carried out afresh with a new, as yet untreated cotton fabric. The DY values are determined as described in Application Example 2.

TABLE 6

| | Bleaching value with $H_2O_2$ (without Mn complex) | Bleaching value with $H_2O_2$ and the 1:1 Mn complex with the ligand L7 | Difference DDY |
|---|---|---|---|
| $1^{st}$ cycle | DY = 14.9 | DY = 23.0 | 8.1 |
| $2^{nd}$ cycle | DY = 11 | DY = 19.0 | 8.0 |

As can be seen from Table 6, the liquors comprising the manganese complex can be used for further bleaching cycles without any appreciable reduction in the bleaching action.

Application Example 7

Catalytic Bleaching of Cellulose 20 g of cellulose [TPP-CT CSF129, Ref. No. P-178635 (ISO 57.4)] are steeped in a litre of water for 65 hours and then stirred in a mixer for 2 minutes to give a paste-like pulp. A bleaching bath containing 50 g of the pulp so prepared in 180 ml of water, 100 μM of Dequest 2041 (sequestering agent), 8.6 mM of hydrogen peroxide and 20 μM of catalyst from Example 35 is maintained at 40° C. for 30 minutes. At the same time 1N sodium hydroxide solution is metered-in in such a manner that a pH of 10.0 is maintained. Filtration and air-drying are then carried out. A sample that has been compressed to form a circular sheet of 10 cm diameter is then tested for the lightness Y obtained (according to CIE, reflectance spectroscopy). The results are compiled in the following Table.

TABLE 7

|  | Lightness Y |
| --- | --- |
| Test sample, untreated | 63.4 |
| Test sample, catalytically bleached | 66.9 |

Application Example 8

Action as Catalyst for DTI (Dye Transfer Inhibition)

In accordance with this application, the redeposition of dyes in washing liquors, especially, should be avoided.

7.5 g of white cotton fabric are treated in 80 ml of washing liquor. The liquor contains a standard washing agent (ECE, 456 IEC) in a concentration of 7.5 g/l. The hydrogen peroxide concentration is 8.6 mmol/l. The catalyst concentration (of manganese(II) chloride tetrahydrate with the ligand, prepared in methanolic solution with the addition of a small amount of lithium hydroxide) is 50 µmol/l, and a solution of the test dye Direct Brown 172 having 10 mg/l of the 250% formulation. The washing process is carried out in a steel beaker in a LINITEST apparatus for 30 minutes at 40° C. For testing the activity of the catalysts, the DTI activity is determined. The DTI (Dye Transfer Inhibition) activity a is defined as the following percentage.

$$a=([Y(E)-Y(A)]/[Y(W)-Y(A)])*100$$

where Y(W), Y(A) and Y(E) are the CIE lightness values of the white material, of the material treated without the addition of catalyst and of the material treated with the addition of catalyst, in that order. a=0 denotes a completely inactive product, the addition of which to the washing liquor does not prevent dye transfer, whereas a=100% corresponds to a perfect catalyst which totally prevents the staining of the white material. The reflection spectra of the samples were measured using a SPECTRAFLASH 2000 and converted into lightness values (D65/10) in accordance with a standard CIE procedure.

A 1:1 manganese complex with ligand L7 gives a value of a=90% in accordance with the test procedure described above.

Application Example 9

The use of the catalysts according to the invention causes hardly any additional fading of the dyes in dyed cotton laundry. When used as described above in Application Example 8, after treatment five times, on average, virtually no losses of dye are recorded. The values given in the following Table are relative percentage dye losses, determined on the basis of Kubelka-Munk values at the respective absorption maximum.

TABLE 8

| Cotton dyeing with dye | Dye loss (%) in system | |
| --- | --- | --- |
|  | with Mn-L7 (50 µM) | without catalyst |
| Cibanone Brown BR | 0 | 0 |
| Cibanone Blue RS | 3 | 2 |
| Procion Brown H-4RD | 9 | 11 |
| Levafix Scarlet E-2GA | 10 | 10 |

Application Example 10

Catalytic Action for the Epoxidation of Olefins 17 mg (0.05 mmol) of 2-[(2-hydroxy-ethyl)-[2,2';6',2'']terpyridin-4'-yl-amino]-ethanol (L7, Example 7), 10 mg (0.04 mmol) of manganese(II) acetate tetrahydrate and 0.32 mmol of sodium ascorbate are added to a solution of 1.09 ml (10 mmol) of ethyl acrylate in 0.5 ml of acetonitrile. The mixture is cooled in an ice bath and a 30% strength hydrogen peroxide solution (2.27 g, 20 mmol) is added dropwise thereto in the course of 20 minutes. The mixture is then left for 14 hours at room temperature, then diluted with diethyl ether and the phases are separated. The organic extract is dried over sodium sulfate, filtered and concentrated. The catalytic turnover number for the epoxide formed, ethyl oxirane-2-carboxylate, is determined by comparing the intensity of the epoxide methine proton at 3.34-3.38 ppm with the ligand signal L7 at 8.53 ppm as reference and is 35±8. Ethyl oxirane-2-carboxylate, epoxide signals $^1$H-NMR (360 MHz, CDCl$_3$): 2.68-2.89 (m, 2H, CH$_2$); 3.34-3.38 (m, 1H, CH). Without the addition of ligand, epoxide cannot be detected. (see in this connection also Berkessel, A. et al., Tetrahedron Lett. 1999, 40, 7965-7968).

What is claimed is:

1. A method of carrying out an oxidation reaction which comprises bringing an oxidizable substrate into contact with a metal complex compound of formula (1), wherein an oxidizingly effective amount of said metal complex is incorporated into a washing, cleaning, disinfecting or bleaching agent as a catalyst for said oxidation reaction, $$[L_nMe_mX_p]^zY_q \qquad (1),$$

wherein Me is manganese,

X is $CH_3CN$, $H_2O$, $F^-$, $Cl^-$, $Br^-$, $HOO^-$, $O_2^{2-}$, $O^{2-}$, $R_{17}COO^-$, $R_{17}O^-$, LMeO$^-$ or LMeOO$^-$ wherein R$_{17}$ is hydrogen or unsubstituted or substituted $C_1$-$C_{18}$alkyl or aryl, n and m are each independently of the other an integer having a value of from 1 to 8, p is an integer having a value of from 0 to 32, z is the charge of the metal complex, Y is $R_{17}COO^-$, $ClO_4^-$, $BF_4^-$, $PF_6^-$, $R_{17}SO_3^-$, $R_{17}SO_4^-$, $SO_4^{2-}$, $NO_3^-$, $F^-$, $Cl^-$, $Br^-$ or $I^-$ wherein R$_{17}$ is hydrogen or unsubstituted or substituted $C_1$-$C_{18}$alkyl or aryl, q =z/(charge Y), and L is a ligand of formula

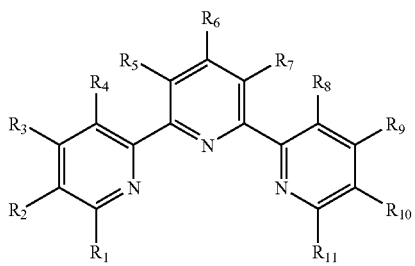

(2)

wherein $R_1$, $R_2$, $R_3$, $R_4$, $R_5$, $R_6$, $R_7$, $R_8$, $R_9$, $R_{10}$ and $R_{11}$ are each independently of the others hydrogen; unsubstituted or substituted $C_1$-$C_{18}$alkyl or aryl; cyano; halogen; nitro; —COOR$_{12}$ or —SO$_3$R$_{12}$ wherein $R_{12}$ is in each case hydrogen, a cation or unsubstituted or substituted $C_1$-$C_{18}$alkyl or aryl; —SR$_{13}$, —SO$_2$R$_{13}$ or —OR$_{13}$ wherein $R_{13}$ is in each case hydrogen or unsubstituted or substituted $C_1$-$C_{18}$alkyl or aryl; —N(R$_{13}$)—NR'$_{13}$R"$_{13}$ wherein $R_{13}$, R'$_{13}$ and R"$_{13}$ are as defined above for $R_{13}$; —NR$_{14}$R$_{15}$ or —N$^\oplus$R$_{14}$R$_{15}$R$_{16}$ wherein $R_{14}$, $R_{15}$ and $R_{16}$ are each independently of the other(s) hydrogen or unsubstituted or substituted $C_1$-$C_{18}$alkyl or aryl, or $R_{14}$ and $R_{15}$ together with the nitrogen atom bonding them form an unsubstituted or substituted 5-, 6- or 7-membered ring which may optionally contain further hetero atoms;

with the proviso that $R_1$, $R_2$, $R_3$, $R_4$, $R_5$, $R_6$, $R_7$, $R_8$, $R_9$, $R_{10}$ and $R_{11}$ are not simultaneously hydrogen.

2. A method according to claim 1, wherein an oxidizingly effective amount of the metal complex compound of formula (1) is formed in situ in the washing, cleaning, disinfecting or bleaching agent.

3. A method according to claim 1, wherein a catalytically effective amount of the metal complex compound of formula (1) is combined with a peroxy compound, and the oxidation reaction is the bleaching of spots or stains on textile material, the prevention of redeposition of migrating dyes in the context of a washing process or the cleaning of hard surfaces.

4. A method according to claim 1, wherein n is an integer having a value of from 1 to 4.

5. A method according to claim 1, wherein m is an integer having a value of 1 or 2.

6. A method according to claim 1, wherein p is an integer having a value of from 0 to 4.

7. A method according to claim 1, wherein z is an integer having a value of from 8$^-$ to 8$^+$.

8. A method according to claim 1, wherein aryl is phenyl or naphthyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthoxy.

9. A method according to claim 1 wherein the 5-, 6- or 7-membered ring formed by $R_{14}$ and $R_{15}$ together with the nitrogen atom bonding them is an unsubstituted or $C_1$-$C_4$alkyl-substituted pyrrolidine, piperidine, piperazine, morpholine or azepane ring.

10. A method according to claim 1, wherein $R_6$ is $C_1$-$C_{12}$alkyl; phenyl unsubstituted or substituted by $C_1$-$C_4$alkyl, $C_1$-$C_4$alkoxy, halogen, cyano, nitro, carboxyl, sulfo, hydroxyl, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthoxy; cyano; halogen; nitro; —COOR$_{12}$ or —SO$_3$R$_{12}$ wherein $R_{12}$ is in each case hydrogen, a cation, $C_1$-$C_{12}$alkyl, or phenyl unsubstituted or substituted as indicated above; —SR$_{13}$, —SO$_2$R$_{13}$ or —OR$_{13}$ wherein $R_{13}$ is in each case hydrogen, $C_1$-$C_{12}$alkyl, or phenyl unsubstituted or substituted as indicated above; —N(R$_{13}$)—NR'$_{13}$R"$_{13}$ wherein $R_{13}$, R'$_{13}$ and R"$_{13}$ are as defined above for $R_{13}$; —NR$_{14}$R$_{15}$ or —N$^\oplus$R$_{14}$R$_{15}$R$_{16}$ wherein $R_{14}$, $R_{15}$ and $R_{16}$ are each independently of the other(s) hydrogen, unsubstituted or hydroxyl-substituted $C_1$-$C_{12}$alkyl, or phenyl unsubstituted or substituted as indicated above, or $R_{14}$ and $R_{15}$ together with the nitrogen atom bonding them form an unsubstituted or $C_1$-$C_4$alkyl-substituted pyrrolidine, piperidine, piperazine, morpholine or azapane ring.

11. A method according to claim 10, wherein the ligand L is a compound of formula

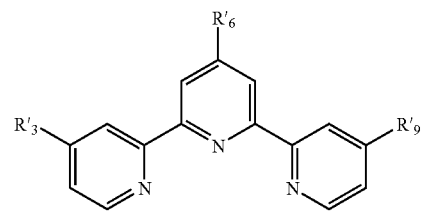

(3)

wherein

R'$_3$, R'$_6$ and R'$_9$ are as defined for $R_6$ in claim 10.

12. A method according to claim 11, wherein

R'$_3$, R'$_6$ and R'$_9$ are each independently of the others $C_1$-$C_4$alkoxy; hydroxy; phenyl unsubstituted or substituted by $C_1$-$C_4$alkyl, $C_1$-$C_4$alkoxy, phenyl or by hydroxy; hydrazino; amino; N-mono- or N,N-di-$C_1$-$C_4$alkylamino unsubstituted or substituted by hydroxy in the alkyl moiety; or an unsubstituted or $C_1$-$C_4$alkyl-substituted pyrrolidine, piperidine, piperazine, morpholine or azepane ring.

13. A method according to claim 10, wherein $R_6$ is hydroxy.

14. A method according to claim 1, wherein Me is manganese which is present in oxidation state II, III, IV or V.

* * * * *